United States Patent [19]
Masinovsky et al.

[11] Patent Number: 5,827,670
[45] Date of Patent: Oct. 27, 1998

[54] METHODS OF ISOLATING AND DETECTING BONE MARROW STROMAL CELLS WITH VCAM-1-SPECIFIC ANTIBODIES

[75] Inventors: Boris Masinovsky, Bellevue; William Michael Gallatin, Mercer Island; Paul J. Simmons, Seattle, all of Wash.

[73] Assignee: Fred Hutchinson Cancer Research Center, Seattle, Wash.

[21] Appl. No.: 480,840

[22] Filed: Jun. 7, 1995

Related U.S. Application Data

[62] Division of Ser. No. 448,649, May 24, 1995, which is a continuation of Ser. No. 51,445, Apr. 21, 1993, abandoned, which is a division of Ser. No. 562,008, Aug. 2, 1990, Pat. No. 5,206,345.

[51] Int. Cl.$^6$ .................................................. G01N 33/53
[52] U.S. Cl. ............................................. 435/7.21; 435/2
[58] Field of Search ............................. 424/130.1, 134.1, 424/140.1, 143.1, 152.1, 153.1, 172.1, 173.1; 435/2, 7.21, 7.24, 325, 372; 530/388.2, 388.22, 388.7

[56] References Cited

U.S. PATENT DOCUMENTS

| | | | |
|---|---|---|---|
| 4,803,072 | 2/1989 | Dalton et al. | 424/85.5 C |
| 4,851,220 | 7/1989 | Yim et al. | 424/85.7 |
| 4,868,119 | 9/1989 | Clark et al.. | 435/240.2 |
| 4,894,226 | 1/1990 | Aldwin et al. | 424/85.2 |
| 4,908,433 | 3/1990 | Mertelsmann et al. | 530/351 |
| 5,011,778 | 4/1991 | Newman et al. | 435/240.27 |
| 5,272,263 | 12/1993 | Hession et al. | 536/23.5 |

FOREIGN PATENT DOCUMENTS

| | | |
|---|---|---|
| 302 429 A1 | 2/1989 | European Pat. Off.. |
| 408 859 A2 | 1/1991 | European Pat. Off.. |
| 410 750 A2 | 1/1991 | European Pat. Off.. |
| 505 749 A2 | 9/1992 | European Pat. Off.. |
| WO 90/07932 | 7/1990 | WIPO. |
| WO 90/13300 | 11/1990 | WIPO. |
| WO 91/05038 | 4/1991 | WIPO. |
| WO 91/07186 | 5/1991 | WIPO. |
| WO 91/14450 | 10/1991 | WIPO. |
| WO 92/00751 | 1/1992 | WIPO. |
| WO 92/03139 | 3/1992 | WIPO. |
| WO 92/11030 | 7/1992 | WIPO. |
| WO 92/12994 | 8/1992 | WIPO. |
| WO 93/19770 | 10/1993 | WIPO. |

OTHER PUBLICATIONS

1. Dittel et al. Blood 81: 2272–2282 (1993).
2. Wilkens et al. J. Pathol. 177: 295–301 (1995).
3. Ryan et al. J. Clin. Invest. 88: 995–1004 (1991).
4. Jacobsen et al. Blood 87: 73–82 (1996).
1. Paul (Ed.) Fundamental Immunology Reven Probe p. 242 only NY 1993.
2. Liesverd et al. Blood 81: 112–121 (1993).
Ager, A., "Isolation and culture of high endothelial cells from rat lymph nodes," *J. Cell. Sci.*, 87:133–144, (1987).

Bentley, S.A., "Close range cell: cell interaction required for stem cell maintenance in continuous bone marrow culture," *Exp. Hematol.*, 9:308–312, (1981).
Bevilacqua, M.P. et al., "Interleukin 1 acts on cultured human vascular endothelium to increase the adhesion of polymorphonuclear leukocytes, monocytes, and related leukocyte cell lines," *J. Clin. Invest.* 76:2003–2011, (1985).
Bevilacqua, M.P. et al., "Indentification of an inducible endothelial–leukocyte adhesion molecule," *Proc. Natl. Acad. Sci., USA*, 84:9238–9242, (1987).
Broxmeyer, H.E. et al., "Synergistic effects of purified recombinant human and murine B cell growth factor–1/IL–4 on colony formation in vitro by hemopoietic progenitor cells," *J. Immunol.*, 141:3852–3862, (1988).
Carlos et al., "Vascular Cell Adhesion Molcule–1 mediates Lymphocyte adherence to cytokine–activated cultured human endothelial cells", *Blood*, 76:965–970 (1990).
Carter et al., "The induction of protective immunity to *Leishmania major* in the BALB/c mouse by Interleukin 4 treatment", *Eur. J. of Immunol.*, 19:779–782 (1989).
Cavender, D.E. et al., "Interleukin 1 increases the binding of human B and T lymphocytes to endothelial cell monolayers," *J. Immunol.*, 136:203–207, (1986).
Calvender, D.E. et al., "Stimulation of endothelial cell binding of lymphocytes by tumor necrosis factor," *J. Immunol.*, 139:1855–1860, (1987).
Civin C.I. et al., "Antgenic analysis of hematopoiesis, III. A hematopoietic progenitor cell surface antigen defined by a monoclonal antibody raised against KG–1a cells," *J. Immunol.*, 133:157–165, (1984).

(List continued on next page.)

*Primary Examiner*—Lila Feisee
*Assistant Examiner*—Phillip Gambel
*Attorney, Agent, or Firm*—Marshall, O'Toole, Gerstein, Murray & Borun

[57] ABSTRACT

A therapeutic method of modulating the immune response, by administering to a patient an amount of IL-4 effective to promote peripheral blood lymphocyte adhesion to microvascular endothelial cells in lymphoid organs. The IL-4 is preferably coadministered with IL-1β.

An improved method of screening a cell line for the production of a binding partner that binds with a cell adhesion molecule, by contacting the binding partner with IL4-activated and nonactivated microvascular endothelial cells, and selecting binding partners that bind to the IL4-activated microvascular endothelial cells but not to the nonactivated microvascular endothelial cells. The selected binding partners may thereafter be tested for the ability to block lymphocyte binding to cytokine-activated endothelial cells. The binding partners are preferably also characterized by binding to human VCAM-1 and to IL4- or TNFα-activated bone marrow stromal cells. A representative embodiment is mAb 6G10 produced by hybridoma ATTC No. HB 10519.

A therapeutic method of modulating the immune response in a patient, by administering to the patient an agent that specifically binds to IL4-activated microvascular endothelial cells, in an amount effective to impede transmigration of lymphocytes that specifically bind to VCAM-1 from blood across postcapillary venules.

4 Claims, 12 Drawing Sheets

OTHER PUBLICATIONS

Collins, T. et al., "Recombinant human tumor necrosis factor increases mRNA levels and surface expression of HLA–A,B antigens in vascular endothelial cells and dermal fibroblasts in vitro," *Proc. Natl. Acad. Sci, USA*, 83:446–450, (1986).

Cotran, R.S., "New roles for the endothelium in inflammation and immunity," *Am. J. Pathol.*, 129:407–413, (1987).

Damle, N.K. and L.V. Doyle, "Ability of human T lymphocytes to adhere to vascular endothelial cells and to augment endothelial permeability to macromolecules is linked to their state of post–thymic maturation," *J. Immunol.*, 144:1223–1240, (1990).

Dexter, T.M. et al., "Conditions controlling the proliferation of haemopoietic stem cells in vitro," *J. Cell. Physiol*, 91:335–344, (1977).

Duijvestijn, A.M. et al., "Interferon–γ regulates an antigen specific for endothelial cells involved in lymphocyte traffic," *Proc. Natl. Acad. Sci. USA*, 83:9114–9118, (1986).

Duijvestijn, A., and A. Hamann, "Mechanisms and regulation of lymphocyte migration," *Immunol. Today*, 10:23–28, (1989).

Dustin, M.L. and T.S. Springer, "Lymphocyte function–associated antigen–1 (LFA–1) interaction with intercellular adhesion molecular–1 (ICAM–1) is one of least three mechanisms for lymphocyte adhesion to cultured endothelial cells," *J. Cell Biol.*, 107:321–331, (1988).

Edgington, "How Sweet It Is: Selectin–Mediating Drugs," *Biotechnology* 10:383–389 (1992).

Elias, J.A. et al., "A synergistic interaction of IL–6 and IL–1 mediates the thymocyte–stimulating activity produced by recombinant IL–1 stimulated fibroblasts," *J. Immunol.* 142:509–514, (1989).

Elices, M.J. et al., "VCAM–1 on activated endothelium interacts with the leukocyte integrin VKA–4 at a site distinct from the VLA–4/fibronectin binding site," *Cell*, 60:577–584, (1990).

Essner et al., "IL–4 down–regulates IL–1 and TNF gene expression in human monocytes", *J. Immunol.*, 142:3857–3861 (1989).

Galea, "Increased Lymphocyte Adhesion to Allogeneic Cells by Interleukin–4 (IL–4)", *Transplantation Proceedings*, 23:243–244 (1991).

Gallatin, W.M. et al., "A cell–surface molecule involved in oragan–specific homing of lymphocytes," *Nature*, 304:30–34, (1983).

Gallatin, W.M. et al., "Selective replication of simian immunodeficiency virus in a subset of CD4+lymphocytes," *Proc. Natl. Sci. USA*, 86:3301–3305, (1989).

Gallatin, W.M. et al., "Lymphocyte homing receptors," *Cell* 44:673–680, (1986).

Gartner, S. and H.S. Kaplan, "Long–term culture of human bone marrow cells," *Proc. Natl. Acad. Sci, USA*, 77:4756–4759, (1980).

Gillis, "T–Cell–Derived Lymphokines", in *Fundamental Immunology, Second Edition*, Ed. William E. Paul, Raven Press Ltd., NY, pp. 621–638 (1989).

Gimbrone, M.A., Jr. et al., "Endothelial interleukin–8: a novel inhibitor of leukocyte–endothelial interactions," *Science* 246:1601–1603, (1989).

Graber et al. "T Cells Bind to Cytokine–Activated Endothelial Cells Via a Novel, Inducible Sialoglycoprotein and Endothelial Leukocyte Adhesion Molecule–1," *J. Immunol.*, 145:819–830 (1990).

Harlan, "Leukocyte–Endothelial Interactions", *Blood*, 65:513–525 (1985).

Harris et al., "Therapeutic antibodies–the coming of age," *Tibtech* 11:42–44 (1993).

Hart et al., "Potential antiinflammatory effects of interleukin–4: Suppression of human monocyte tmmor necrosis factor α, Interleukin–1, and prostaglandin E2"., *Proc. Nat'l Acad. Sci. of USA*, 86:3803–3807 (1989).

Hemler et al., "Adhesive Protein Receptors on Hematopoietic cells," *Immunol. Today* 9:109–113 (1988).

Hendriks, H.R. et al., "Rapid decrease in lymphocyte adherence to high endothelial venules in lymph nodes deprived of afferent lymphatic vessels," *Eur. J. Immunol.* 17:1691–1695, (1987).

Holzmann, B. et al., "Indentificatin of murine Peyer's patch–specific lymphocyte homing receptor as in integrin molecule with an α chain homologous to human VLA 4α," *Cell* 56:37–46, (1989).

Hughes, C.C.W. et al. "Adhesion of lymphocytes to cerebral microvascular cells: effects of interferon–γ tumour necrosis factor and interleukin–1" *Immunology* 64:677–681, (1988).

Ise, Y. et al., "Molecular mechanisms underlying lymphocyte recirculation. I. Functional, phenotypical and morphological characterization of high endothelial cells cultured in vitro," *Eur. J. Immunol.* 18:1235–1244, (1988).

Issekutz, J. *Immunol.*, "Effects of Six Different Cytokines on Lymphocyte Adherence to Microvascular Endothelium and in vivo Lymphocyte Migration in the Rat" 144:2140–2146. (1990).

Issekutz, T.B. et al., "Role of Interferon in lymphocyte recruitment into the skin," *Cell. Immunol.*, 99:322–333, (1986).

Issekutz, T.B. and J. M. Stoltz, "Stimulation of lymphocyte migration by endotoxin, tumor necrosis factor, and interferon," *Cell Immunol.*, 120:165–173, (1989).

Issekutz, T.B. et la., "Lymphocyte recruitment in delayed–type hypersensitiviy: the role of IFN–γ," *J. Immunol.*, 140:2989–2993, (1988).

Jacobsen et al., "Highly Restricted Expression of a Stromal Cell Determinant in Mouse Bone Marrow In Vivo", *J. Exp. Med.*, 176:927–935 (1992).

Jalkanen, S., et al., "A distinct endothelial cell recognition system that controls lymphocyte traffic into inflamed synovium," *Science*, 233:556–558, (1986).

Kalaaji, A.N. et al., "The enhancement of lymphocyte localization in skin sites of sheep by tumor necrosis factor α," *Immunol. Letters* 23:143–148, (1989/1990).

Kennett, R.H., Fusion Protocols. "Fusion by Centrifugation of Cells Suspended in Polyethylene Glycol," in *Monoclonal Antibodies Hybridomas: a New Dimension in Biological Analysis*, R.H. Kennett et al.: Plenum Press, New York, pp. 35–367, (1980).

Knapp et al., *Leucocyte Typing IV*, Oxford Univ Press, pp. 1083, 1087 only (1989).

Kumar, S. et al., "Heterogeneity in endothelial cells from large vessels and microvessels," *Differentiation* 36:57–70, (1987).

Lapierre, L.A. et al., "Three distinct classes of regulatory cytokines control endothelial cell MHC antigen expression," *J. Exp. Med.* 167:794–804, (1988).

Lewinsohn et al., "Hematopoietic Progenitor Cell Expression of the H–CAM (CD44) Homing–Associated Adhesion Molecule" *Blood* 75:589–595 (1990).

Lowenthal, J.W. et al., "Expression of high affinity receptors for murine interleukin 4 (BSF–1) on hemopoietic and non-hemopoietic cells," *J. Immunol.* 140:456–464, (1988).

Madri, J.A. et al., "Matrix–driven cell size change modulates aortic endothelial cell proliferation and sheet migration," *Am J. Pathol.* 132:18–27, (1988).

Makgoba, M.W. et al., "Functional evidence that intercellular adhesion molecule–1 (ICAM) is a ligand for LFA–1 dependent adhesion T cell–mediated Cytotoxicity," *Eur. J. Immunol.* 18:637–640, (1988).

Marlin, S.D., and T.A. Springer, "Purified intercellular adhesion molecule–1 (ICAM–1) is a ligand for lymphocyte function–associated antigen–1 (LFA–1)," *Cell* 51:813–819, (1987).

Masinovsky et al., "IL–4 Acts Synergistically with IL–1β to Promote Lymphocyte Adhesion to Microvascular Endothelium by Induction of Vascular Cell Adhesion Molecule–1" *Immunol.* 145:2886–2895 (1990).

Masinovsky et al., "Synergistic Effect of Interleukins IL4 and IL1β on Lymphocyte Adhesion to Endothelial Cells" FASEB *Journal* 3(3):A482, Mar. (1989).

McHeyzer–Williams, M.G., "Combination of interleukins 2,4 and 5 regulate the secreation of murine immunoglobulin isotypes," *Eur. J. Immunol.* 19:2025–2030, (1989).

Miyake et al., "Evidence for a Role of the Integrin VLA–4 in Lymphohemopoiesis", *J. Exp Med.*, 173:599–607 (1991).

Monroe, J.G. et al., "Lymphokine regulation of inflammatory process:interleukin–4 stimulates fibroblast proliferation," *Clin. Immunol. Immunopath.* 49:292–298, (1988).

Mountain et al., "Engineering Antibodies of Therapy," *Biotech Ben Eng. Rev.* 10:1–143, (1992).

Munro et al., "Tumor Necrosis Factor and Interferon–γ Induce Distinct Patterns of Endothelial Activation and Associated Leukocyte Accumulation of Skin of *Papio Anubis*," *Amer., J. Pathology*, 135 (1):121–133, (1989).

Noelle, R. et al., "Increased expression of Ia antigens on resting B cells: an additional role for B–cell growth factor," *Proc. Natl. Acad. Sci, USA* 81:6149–6153, (1984).

Ogo et al., "Effects of Interleukin 4 on Stromal Cell–associated Bone Marrow Culture", *Exp. Hematol.*, 19:899–904 (1991).

Oppemheimer–Marks, N., and Ziff, "Migration of Lymphocytes through endothelial cell monolayers: augmentation by interferon–γ," *Cell Immunol.* 114:307–323, (1988).

Osborn, L. et al., "Direct expression cloning of vascular cell adhesion molecule 1, a cytokine–induced indothelial protein that binds to lymphocytes," *Cell* 59:1203–1211, (1989).

Pals, S.T. et al., "Mechanisms of human lymphocyte migration and their role in the pathogenesis of disease," *Immunol. Rev.* 108:111–133, (1989).

Park, L. et al., "Characterization of the human B cell stimulatory factor 1 receptor," *J. Exp. Med.* 166:476–488, (1987).

Park, L.S. et al., "Characterization of the high–affinity cell–surface receptor for murine B–cell–stimulating factor 1," *Proc. Natl. Acad. Sci. USA* 84:1669–1673, (1987).

Paul, W.E. and J. Ohara, "B–cell stimulatory factor 1/interleukin 4," *Ann. Rev. Immunol.* 5:429–459, (1987).

Pelletier et al. "Importance of Endothelial VCAM–1 for Inflammatory Leukocytic Infiltration in Vivo," *J. Immunol.* 149:2473–2481 (1992).

Pober, J.S. "Cytokine–mediated activation of vascular endothelium. Physiology and pathology," *Am. J. Pathol.* 133:426–433, (1988).

Pober, J.S. et al., "Ia expression by vascular endothelium is inducible by activated T cells and human γ–interferon," *J. Exp. Med.* 157:1339–1353, (1983).

Pohlman T.H. and J.M. Harlan, "Human endothelial cell response to lipopolysaccharide, interleukin–1, and tumor necrosis factor is regulated by protein synthesis," *Cell, Immunol.* 119:41–52, (1989).

Rabin, E.M. et al., "Interferon–γ inhibits the action of B cell stimulatory factor (BSF)–1 on resting B cells," *J. Immunol.* 137:1573–1576, (1986).

Zanjani et al., "Human CD34+ Cells Transplanted in Utero in Sheep Fetuses Treated with Anti–Human VLA$_4$ Remain Homeless and Persist in Circulation," *Blood* 84:494a (1994).

Rice et al. "Inducible Cell Adhesion Molecular 110 (INCAM–110) is an Endothelial Receptor for Lymphocytes. A CD11/CD18–independent Adhesion Mechanism," *J Exp. Med.* 171:1369–1374 (1990).

Rice et al., "An inducible endothelial cell surface glycoprotein mediates melanoma adhesion", *Science*, 246:1303–1306 (1989).

Rothlein, R., et al., "A human intercellular adhesion molecule (ICAM–1) distinct from LFA–1," *J. Immunol.* 137:1270–1274, (1986).

Sandmaier et al., "An Antibody That Facilitates Hematopoietic Engraftment Recognizes CD44", *Blood*, 76:630–635 (1990).

Sarvetnick, N. et al., "Insulin–dependent diabetes mellitus induced in transgenic mice by ectopic expression of class II MHC and interferon–gamma," *Cell* 52:773–782, (1988).

Schaffer, "Drug giants, Start–ups target adhesion molecules, key to imflammatory disease," *Biotech. Newswatch:* p. 9 (Oct. 4, 1993).

Schuening, F. et al., "Facilitation of engraftment of DLA–nonidentical marrow by treatment of recipients with monoclonal antibody directed against marrow cells surviving radiation," *Transplantation* 44:607–613, (1987).

Shimizu et al., "Roles of Adhesion Molecules in T–Cell Recognition: Fundamental Similarities between Four Integrins on Resting Human T Cells (LFA–1, VLA–4, VLA–5, VLA–6) in Expression, Binding, and Costimulation," *Immunol. Rev.* 114:109–143 (1990).

Simmons et al., "Vascular Cell Adhesion Molecular–1 Expressed by Bone Marrow Stromal Cells Mediates the Binding of Hematopoietic Progenitor Cells", *Blood*, 80:388–395 (1992).

Simmons et la., "CD34 Expression by Stromal Precursors in Normal Human Adult Bone Marrow", *Blood*, 78:2848–2853 (1991).

Stoolman. L.M., "Adhesion molecules controlling lymphocyte migration," *Cell* 56:907–910 (1989).

Streeter, P.R. et al., "Immunohistologic and functional characterization of vascular addressin involved in lymphocyte homing into peripheral lymph nodes," *J. Cell Biol.* 107:1853–1862, (1988).

Thornhill et al., "IL–4 regulates endothelial cell activation by IL–1, Tumor Necrosis Factor or IFN–gamma", *J. Immunol.*, 145:865–872 (1990).

Thornhill, M.H. et al., "IL–4 increases human endothelial cell adhesiveness for T cells but not for neutrophilis," *J. Immunol.* 144:3060–3065, (1990).

Tsuji, K. et al., "Synergistic action of phorbol ester and IL–3 in the induction of connective tissue–type mast cell proliferation," *J. Immunol.* 144:678–684, (1990).

Vedder et al., "A Monoclonal Antibody to the Adherence–promoting Leukocyte Glycoprotein, CD18, Reduces Organ Injury and Improves Survival from Hemorrhagic Shock and Resuscitation in Rabbits," *J. Clin. Invest.* 81:939–944 (1988).

Vercelli, D. et al., "Il–4 inhibits the synthesis of IFN–gamma and induces the synthesis of IgE in human mixed lymphocyte cultures," *J. Immunol.* 144:570–573, (1990).

Wankowicz, Z. et al. "Synergy between tumor necrosis factor α and interleukin–1 in the induction of polymorphonuclear leukocyte migration during inflammation," *J. Leukoc. Biol.* 43:349–356, (1988).

Wegner et al., "Intercellular Adhesion Molecule–1 (ICAM–1) in the Pathogenesis of Asthma," *Science* 247:456–459 (1990).

Wetzler et al., "Constitutive Expression of Leukemia Inhibitory Factor RNA by Human Bone Marrow Stromal Cells and Modulation by IL–1, TNF–α, and TNF–β",*Exp. Hematol.*, 19:347–351 (1991).

Woodruff, J.J., and L.M. Clarke, "Specific cell–adhesion mechanisms determining migration pathways of recirculating lymphocytes," *Ann. Rev. Immunol.* 5:201–222, (1987).

Yednock, T.A. and S. D. Rosen, "Lymphocyte homing," *Adv. Immunol.* 44:313–378, (1989).

Yu, C.L. et al., "Human gamma interferon increases the binding of T lymphocytes to endothelial cells," *Clin. Exp. Immunol.* 62:554–560, (1985).

Yu, C.L. et al., "Effects of bacterial lipopolysaccharide on the binding of lymphocytes to endothelial cell monolayers." *J. Immunol.* 136:569–573, (1986).

Papayannopoulou et al., "Peripheralization of hemopoietic progenitors in primates treated with anti–VLA$_4$ integrin." *Proc. Natl. Acad. Sci. USA* 90:9374–9378, (1993).

METHODS OF ISOLATING AND DETECTING BONE MARROW STROMAL CELLS WITH VCAM-1-SPECIFIC ANTIBODIES

This is a Divisonal of U.S. application Ser. No. 08/448,649, filed May 24, 1995, which is a Continuation of U.S. application Ser. No. 08/051,455, filed Apr. 21, 1993, now abandoned, which is a Divisonal of U.S. application Ser. No. 07/562,008 filed Aug. 2, 1990, now U.S. Pat. No. 5,206,345.

This invention was made with government support under Public Health Service grants CA40272, P30 CA15704, and RR00166. The government has certain rights in this invention.

TECHNICAL FIELD

This invention relates to genetic engineering involving recombinant DNA technology, and particularly to therapeutic methods and reagents for modulating the immune response including treating inflammation in a patient.

BACKGROUND OF THE INVENTION

The following abbreviations are used in this disclosure: CAM, cell adhesion molecules; EBM, endothelial basal medium; EC, endothelial cells; EDTA, ethylenediaminetetraacetic acid; EGF, epidermal growth factor; ELAM-1, endothelial leukocyte adhesion molecule-1; FBS, fetal bovine serum; HEV, high endothelial venules; HUVEC, human umbilical vein endothelial cells; ICAM-1, intracellular adhesion molecule-1; IL-1, interleukin-1; IL-1β, interleukin-1-beta; IL-4, interleukin-4; INF-γ, interferon-gamma; LDL, low density lipoprotein; LFA-1, lymphocyte function-associated antigen-1; LTBMC, long-term bone marrow culture system; mAb, monoclonal antibody; MLN, mesenteric lymph node; PBL, peripheral blood lymphocytes; PBS, phosphate-buffered saline; PMN, polymorphonuclear leukocyte; SEM, standard deviation; TNF-α, tumor necrosis factor-alpha; VCAM-1, vascular cell adhesion molecule-1; VLA-4, leukocyte integrin VLA-4; WM, Waymouth medium. Throughout the specification, the notation "(#)" is used to refer to the documents listed in the appended Citations section.

Migration of lymphocytes from the bloodstream into surrounding tissues is a dynamic, multistep process initiated by attachment to the luminal surface of endothelial cells (EC) lining the postcapillary venules. Certain components of the microvasculature, notably the morphologically distinct high endothelial venules (HEV) found in lymphoid organs such as lymph nodes, Peyer's patches, and tonsils, continuously support lymphocyte binding and transmigration. Some adhesive interactions attendant with movement into these sites are, at least operationally, organ-specific (1–6). Others are mediated by cell adhesion molecules (CAM) that have more general tissue distributions, for example, ICAM-1/LFA-1 interactions (7–9). During both acute and chronic inflammation, microvascular endothelial cells at other sites can be induced to support traffic of various leukocyte subtypes (5, 10). Accumulation of lymphocytes in chronic inflammations, e.g., arthritic synovia, is usually accompanied by conversion of the local postcapillary venules to a cuboidal morphology and expression of new adhesive structures (3, 5). It has been suggested that lymphocyte adhesion to endothelial cells in chronic inflammatory lesions also incorporates an element of organ- or site-specificity (11). The complete identity and balance of inductive factors in the local microenvironment that contribute to the endothelial-cell "traffic" phenotype, and particularly its organ-specific character at some sites, have yet to be defined in molecular terms. Other factors are likely to be important, e.g., endothelial cell contact with the underlying extracellular matrix (12); but, clearly, release of proinflammatory cytokines in the local milieu contributes markedly to the upregulation of cell adhesion molecules on endothelial cells (13, 14).

For example, interleukin-1 (IL-1), TNF-α, and IFN-γ have all been shown to increase adhesiveness of cultured endothelial cells for granulocytes and lymphocytes (15–23). In some cases these effects are paralleled by enhanced leukocyte migration to sites of cytokine injection in vivo (24, 25). Recently, much progress has been made in identification of specific cell adhesion molecules induced on endothelial cells by proinflammatory cytokines. IL-1, for example, induces endothelial leukocyte adhesion molecule-1 (ELAM-1), a member of the LEC-CAM (Lectin, EGF, Complement-Cellular Adhesive Molecule) family (19, 26), which is selectively adhesive for polymorphonuclear leukocytes and weakly adhesive for monocytes. Similarly, cytokine induction of intercellular adhesion molecule-1 (ICAM-1), a ligand for the leukointegrin LFA-1 (lymphocyte function-associated antigen-1), has been reported on endothelial cells (27). Recently, vascular cell adhesion molecule-1 (VCAM-1) was identified as a TNF- and IL1-inducible ligand for VLA4-mediated attachment of lymphocyte adhesion to human umbilical vein endothelial cells (HUVEC) (28–30). Although not directly linked functionally to lymphocyte transmigration, other cell surface markers associated with traffic endothelium in vivo have been shown to be induced by IFN-γ (15). Additional adhesive ligands of more limited tissue distribution, termed vascular addressing, MECA-79 and MECA-367, have been identified in lymph nodes and mucosal lymphoid tissues, respectively (31, 32). Whether these ligands can be induced in vitro by specific cytokines is not known at this point, but studies of transgenic mice suggest that IFN-γ may contribute to their expression in vivo (33).

The capacity of cytokines to enhance lymphocyte adhesion to microvascular-derived endothelial cells has been analyzed in rodents and sheep (15, 24, 25). In humans, wherein most of the molecular definition of EC-CAM exists, cytokine induction has been studied almost exclusively using umbilical vein as the endothelial cell source (16–19). As pointed out recently by Issekutz (24), certain disparities exist between results obtained in these systems.

Because of this and since our preliminary results indicated that large-vessel-and microvascular-derived endothelial cells might differ in cytokine responses vis-a-vis adhesive events, we endeavored to test how immunologically active cytokines affected lymphocyte adhesion to primate (macaque) microvascular endothelial cells. Further, since there have been suggestions of cytokine dependence for the traffic endothelial cell phenotype not only at sites of inflammation, but also for high endothelium in lymph nodes (34), mesenteric lymph nodes were used as one source of microvascular endothelial cells.

SUMMARY OF THE INVENTION

Our results indicate that IL1β- and IFNγ-induced microvascular endothelial cells behave similarly to HUVEC. In contrast, IL-4 on its own, and in combination with IL-1β, was a potent effector of lymphocyte adhesion to microvascular endothelial cells, but had only minimal effects on umbilical-vein-derived endothelial cells. A significant portion of the increased adhesion was due to upregulated expression of VCAM-1 or a serologically related molecule.

The invention accordingly provides, in one aspect, a therapeutic method of modulating the immune response in a patient, by administering to the patient an amount of IL-4 effective to promote peripheral blood lymphocyte adhesion to microvascular endothelial cells in lymphoid organs and thereby modulate the patient's immune response. The IL-4 is preferably coadministered with IL-1β to the patient. In a representative embodiment, IL-4 is administered to a patient needing treatment for inflammation, to promote transmigration of lymphocytes from blood across postcapillary venules at sites of inflammation in the patient.

Another aspect of the invention is the provision of an improved method of screening a cell line for the production of a binding partner that binds with a cell adhesion molecule. The method includes the steps of contacting the binding partner with cells bearing the cell adhesion molecule and detecting any binding reaction between the binding partner and the cells. The improvement involves contacting the binding partner with IL4-activated and nonactivated microvascular endothelial cells, and selecting cell lines that produce binding partners that bind to the IL4-activated microvascular endothelial cells but not to the nonactivated microvascular endothelial cells. As an additional screening step, the binding partners of the selected cell lines may thereafter be tested for the ability to block lymphocyte binding to cytokine-activated endothelial cells. In this manner, the invention provides immunological and peptide binding partners that specifically bind to IL4-activated but not nonactivated microvascular endothelial cells. The binding partners are preferably also characterized by the ability to block lymphocyte binding to cytokine-activated endothelial cells, and most preferably by binding to human VCAM-1 and to IL4- or TNFα-activated bone marrow stromal cells. A representative embodiment of this most preferred binding partner is mAb 6G10 produced by hybridoma ATCC No. HB 10519.

In a related aspect, the invention provides a therapeutic method of modulating the immune response in a patient, by administering to the patient an agent that specifically binds to IL4-activated microvascular endothelial cells, in an amount effective to impede transmigration of cells, such as lymphocytes or tumor cells, that specifically bind to VCAM-1 from blood across postcapillary venules into extracellular fluid in the patient.

DETAILED DESCRIPTION OF THE PREFERRED EMBODIMENT

Figure 1A:
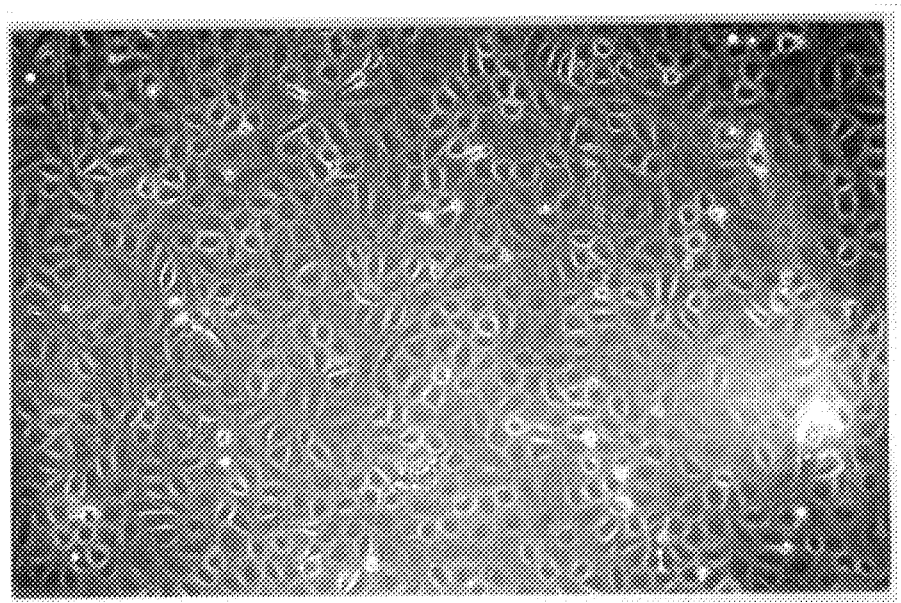
FIG. 1 shows photomicrographs of representative microvascular endothelial cells cultured in serum-containing (panel A) and serum-free media (panel B), as described in Example 1.

Adhesion of lymphocytes to endothelial cells (EC) is the requisite first element in the multistep process of transmigration from blood across the postcapillary venules. Selective expression of cell adhesion molecules (CAM) by microvascular endothelial cells in lymphoid organs (e.g., lymph nodes) and during tissue inflammation modulates this traffic in a site-directed manner. CAM synthesis by endothelial cells is regulated in turn by cytokines released in the local microenvironment. Studies done largely with human umbilical vein endothelial cells (HUVEC) have implicated IL-1, IFN-γ, and TNF-α as cytokines that promote leukocyte adhesion to endothelial cells. In the work reported here, the responses of cultured microvascular endothelial cells derived from macaque lymph nodes to IL-1β, IL-2, and IL-4 were examined. Increases in lymphocyte adhesion following preculture of microvascular endothelial cells in IL-1β or IFN-γ were typically two-to fourfold above controls and comparable to those reported for HUVEC. IL-2 had no effect. The most striking finding followed stimulation with IL-4. While only marginal effects on large vessel cultured endothelial cells were seen, this cytokine markedly enhanced adhesion to microvascular endothelial cells. IL-4 induced adhesion was observed as early as 4 hours after induction, plateaued by 24 hours, was stable through 72 hours of culture, but decayed to basal levels within 72 hours after removal of IL-4 from the cultures. IL-1β, but not IL-2 or IFN-γ, synergistically enhanced the action of IL-4 on cultured microvascular endothelial cells to promote lymphocyte binding. Adhesion triggered in this manner required de novo protein synthesis. However, the avidity of IL4-activated microvascular endothelial cells for lymphocytes, and analyses of kinetics, cation and temperature dependence, and/or lack of blockade with mAb's to ELAM-1, ICAM-1, and MECA-79 indicated that these CAM were not central to the phenomenon. To aid identification of the relevant CAM, mAb's specific to IL4-induced microvascular endothelial cells were produced. One of these, 6G10, blocked up to 90% of lymphocyte adhesion to IL4-induced microvascular endothelial cells and reacted specifically with CHO cells transfected with human VCAM-1, an endothelial ligand of the β1 integrin, VLA-4. Our results indicate that IL-4 may have potent effects on lymphocyte recirculation in vivo and that endothelial cell subtypes may regulate VCAM-1 differentially in response to specific cytokines.

Numerous studies suggest that recruitment of leukocytes to sites of both acute and chronic inflammation is triggered by increased expression and function of cell adhesion molecules (CAM) on endothelium as well as on blood leukocytes (3, 10, 14). That elevated CAM function is accomplished in part by release of proinflammatory cytokines such as IL-1, IFN-γ, and TNF-α is also well documented in the recent literature (11, 13, 23, 28). Other elements of the complex process of vessel transmigration, lateral movement on the endothelial surface, and diapedesis, for example, are undoubtedly facilitated or inhibited by other cytokines, e.g., IL-8 (51). Moreover, some endothelial CAM are more adhesive in vitro for certain leukocyte subpopulations than others (17, 19, 52). Also, kinetics of individual CAM expression may differ, and their induction by individual cytokines may be selective. Therefore, local secretion of these soluble molecules could provide a means whereby the influx of lymphoid; monocytic, and granulocytic cells could be regulated with a degree of independence.

The studies reported here were undertaken because of dissimilarities between some of the in vitro data on leukocyte adhesion to cytokine-stimulated endothelium and in vivo findings on recruitment to sites of cytokine injection. For example, while IFN-γ markedly stimulates lymphocyte migration to skin after local injection (23, 53, 54), significant but less striking effects on lymphocyte adhesion to cultured human endothelium were reported (20, 27). Reciprocally, IL-1, which stimulates adhesion well in vitro, did not enhance recruitment to skin at injection sites in rats (23, 54). In principle, these disparate observations could be explained by species-specific differences since most in vitro studies have used human umbilical vein endothelial cells as the cellular substrate for adhesion, while in vivo experiments have typically utilized rodent or ovine models (24, 25). Alternatively, distinctions between microvascular and large vessel derived endothelial cells could be responsible. For example, Issekutz (24) and Hughes et al. (55) did find that IFN-γ treatment of rat microvascular endothelial cells significantly increased the binding of lymphocytes. An additional explanation for the disparity between in vivo and in vitro data suggested by the work of Oppenheimer-Marks and Ziff (56) is that IFN-γ promotes both adhesion and subsequent migration across endothelium, while IL-1 may only stimulate the initial lymphocyte binding. To help resolve some of these issues, we developed a system to examine adhesion of lymphocytes to cultured lymph node microvascular endothelium. Relatively pure cultures of endothelial cells were propagated from macaque lymph nodes as disclosed below. These cultured cells had the characteristic dome-shaped, cobblestone morphology of cultured endothelial cells and expressed markers characteristic of endothelium, such as uptake of acetylated-LDL. Our results are summarized in Table 1.

TABLE 1

Effect of cytokines on cultured microvascular endothelium.

| Medium | Cytokine(s) | none | IL-1β | IL-2 | IFN-γ |
|---|---|---|---|---|---|
| Complete EBM (2% FBS) | none | 44.5 ± 12.0 | 188 ± 21.9 | 46.0 ± 6.9 | 65.5 ± 14.8 |
|  | IL-4 | 200 ± 37.2 | 615 ± 74.4 | 230 ± 57.5 | 251 ± 22.0 |
| Complete CS-1.55 | none | 250 ± | 656 ± | 291 ± | 452 ± |

TABLE 1-continued

Effect of cytokines on cultured microvascular endothelium.

| Medium | Cytokine(s) | none | IL-1β | IL-2 | IFN-γ |
|---|---|---|---|---|---|
| (serum-free) |  | 53.7 | 67.7 | 57.8 | 36.9 |
|  | IL-4 | 684 ± 48.4 | 1226 ± 99.3 | 633 ± 88.2 | 856 ± 107.2 |

Endothelial cells were treated with IL-1β (1 ng/ml), IL-2 (100 u/ml), IL-4 (10 ng/ml), IFN-γ (100 u/ml), or their combination, or left unstimulated for 24 hr as indicated. After removal of cytokines, PBL were added to each well, the adhesion assay was performed (constant agitation for 30 min at +4° C.) and lymphocytes bound to endothelial cells were counted. Each value represents a mean number of adherent lymphocytes per $mm^2$ ± SEM.

In general, the results for IL-1β, IFN-γ, and IL-2 were similar to those reported previously for HUVEC. Both IL-1β and IFN-γ stimulated lymphocyte adhesion, albeit more strongly and consistently in the case of IL-1β, while IL-2 was without any noticeable effect. The most striking finding was that IL-4 treatment of endothelial cells markedly increased their adhesiveness for lymphocytes. This was apparent as early as 4 hours after treatment, reached a plateau by approximately 12–24 hours, and was maintained for at least 72 hours. The effect required de novo protein synthesis and continued presence of cytokines for maintenance. Interestingly, this robust effect of IL-4 was not observed on HUVEC, or on endothelial cells from macaque aorta; in these cases IL-4 had either no effect or only marginally enhanced lymphocyte adhesion (J. Harlan, J. Pober, personal communications; Masinovsky and Gallatin, unpublished data). Typically, the maximal increase over background in lymphocyte adhesion was in the same range (approximately twofold) as that reported recently for IL4-treated HUVEC by Thornhill et al. (52). The mechanisms underlying this differential response of the two endothelial cell types is not known. However, it is probably not explained by a relative absence of IL-4 receptors per se on HUVEC. In macaque, at least, IL-4 receptor expression on large vessel and microvascular endothelial cells is roughly equivalent (Masinovsky and Beckmann, unpublished data).

The involvement of LFA-1/ICAM-1 mediated adhesion, at least as an obligatory part of this phenomenon, could be excluded because the IL4-induced binding was: a) not sensitive to cold temperature, b) primarily calcium dependent, and c) not blocked by addition of mAb to these CAM. Similar antibody inhibition tests excluded a necessary involvement of MECA-79, CD44, and class II MHC in the process. Although not directly excluded, the utilization of ELAM-1 as an adhesive component seems unlikely. Kinetics of its induction versus the adhesion observed here are different, and ELAM-1 is preferentially adhesive for neutrophils and monocytes rather than for lymphoid cells. The fact that one mAb, 6G10, specifically reactive with IL4-induced microvascular endothelial cells, blocked lymphocyte adhesion and reacted selectively with human VCAM-1 transfectants strongly suggests that VCAM-1 or a serologically closely related molecule (of 100–110 kD, see below) mediates lymphocyte binding in this system. It might not be the only relevant structure since other cell surface molecules were induced by IL-4 on microvascular endothelial cells (Masinovsky and Gallatin, unpublished data). However, the identification of these additional components, as cell-adhesion molecules, has not been established.

VCAM-1, also known as INCAM-110, was recently identified on TNF-α- and IL1-induced HUVEC (28, 29). Molecular analyses reveal that it is a member of the immunoglobulin supergene family and has as one ligand the β1-integrin, VLA-4 (29, 30). Although its precise physiologic role during inflammation has yet to be defined, recruitment of lymphocytes to chronic inflammations such as arthritic synovia is one possibility. Involvement of VCAM-1, or a related molecule, in normal traffic through mucosal lymphoid tissue may also occur since the α-chain of VLA-4 has been implicated in lymphocyte binding to high endothelium in Peyer's patches (2). VCAM1-mediated adhesion may selectively recruit only certain lymphocyte subsets since VLA-4 expression is not uniform on all peripheral lymphocytes. In fact, direct evidence for lymphocyte subset biased adhesion to cytokine activated endothelium was provided recently by Damle and Doyle (57). The involvement of VLA-4/VCAM-1 mediated adhesion was not tested in their study, but this would be an intriguing possibility that could explain their data in part. In addition to its function in lymphoid traffic, VCAM-1 may also be an important factor in tumor metastasis (28). Unfortunately, other mAb's currently available to VCAM-1 react poorly with nonhuman primate endothelial cells (Masinovsky and Gallatin, unpublished data; M. Bevilacqua, J. Harlan, J. Pober, personal communication). Since mAb 6G10 reacted with both human and macaque endothelial cells it should provide a useful tool to address the issues of tissue distribution, in vivo function, and the role of IL-4 in VCAM-1 induction. For example, tests to determine if systemic administration of IL-4 results in VCAM-1 induction could provide insight into the mechanisms underlying vascular leakage and the lymphocytopenia observed during clinical therapy with this cytokine.

That IL-4 may regulate lymphocyte traffic is perhaps not surprising in hindsight. Originally described as a B cell stimulant (58), IL-4 has receptors on a variety of cell types, including nonhemopoietic cells (41–44), and triggers many distinct responses. IL-4 promotes adhesion between B and T cells, in part by upregulation of class II MHC molecules (59). That IL-4 acted synergistically with IL-1β to activate microvascular endothelial cells is a novel finding but not without precedent. IL-4 acts together with IL-2 and IL-5 to regulate secretion of different immunoglobulin isotypes (60), with GCSF to promote granulopoeisis (46), and with IL-3 to regulate the differentiation of mast cells (61). Similarly, synergy between IL-1 and TNF has been reported in inducing migration of PMNs during inflammation (62). Although antagonism between IL-4 and IFN-γ has been reported during B cell activation (63, 64), we did not observe an effect of this type on cultured endothelial cells (Table 1). The mechanism underlying synergy between IL-1 and IL-4 in this system is at present unknown. While not formally excluded, it seems unlikely that either cytokine exerts its effect solely through induction of the other. When tested alone over a wide range of concentrations, neither cytokine induced as much adhesion as when the two were applied together. Nonetheless, it will be interesting to determine if either IL-4 or TNF-α, which are both good inducers of VCAM-1, act directly on endothelial cells or indirectly through induction of a second soluble mediator.

EXAMPLE 1
Propagation of microvascular endothelial cells

Figure 1B:
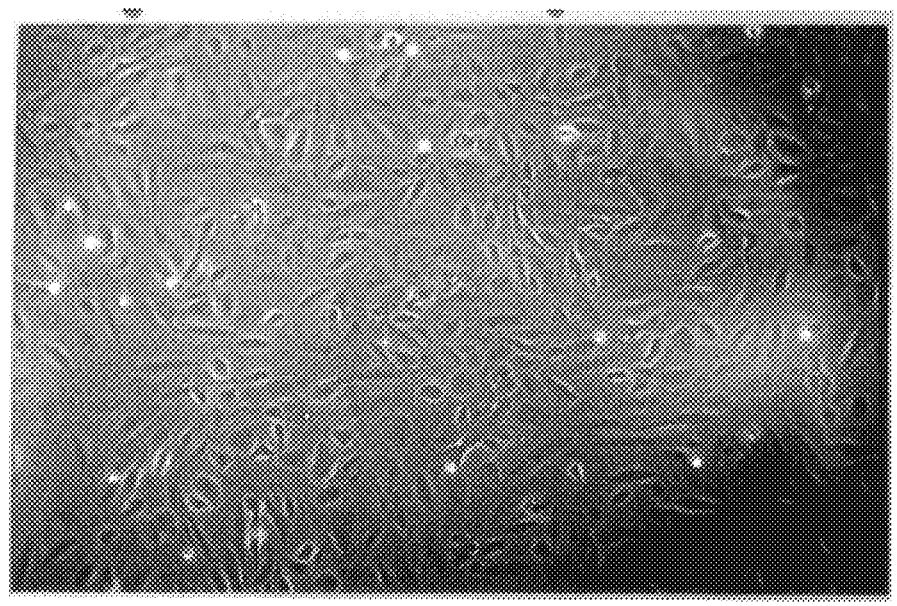

To initiate this work, a procedure for obtaining uniform cultures of endothelial cells from lymph nodes was derived. Small colonies with endothelial morphology in cultures prepared from macaque mesenteric lymph nodes, as outlined in the appended Materials and Methods section, were recognized 2–3 days after primary plating. Cells had a polygonal shape with few contacts between them. By the 5th to 7th day the cultures grew to confluency, most of the growth occurring at the periphery of the colony, at which point the first selective removal of fibroblasts and other nonendothelial cells was carried out by limited trypsinization. When combined with selective growth media, this procedure typically yielded cultures which were virtually free of contamination by cells having a fibroblastoid morphology or markers characteristic of dendritic or monocytic cells. Although endothelial cells were successfully grown in all three of the media preparations used, the media varied in their relative capacities to selectively propagate endothelial cells maintaining typical endothelial markers and cytokine responses (see below). For example, morphological differences were observed between microvascular endothelial cells grown in different media, with serum-containing media giving a higher frequency of cells having a cobblestone morphology characteristic of endothelial cells (FIG. 1, panel A). Reciprocally, the most rapid and selective growth of endothelial cells compared to nonendothelial cells was obtained with the serum-free CS-1.55 medium (panel B).

Referring to FIG. 1 in more detail, the two photomicrographs, of live cultured microvascular endothelium of macaque mesenteric lymph nodes, show the dome-shaped appearance of cells grown to confluency in complete EBM containing 2% FBS (panel A), as compared to the more elongated cells in serum-free endothelial cell medium, complete CS-1.55 (panel B). Scale bars indicate 100 μm.

Figure 2:
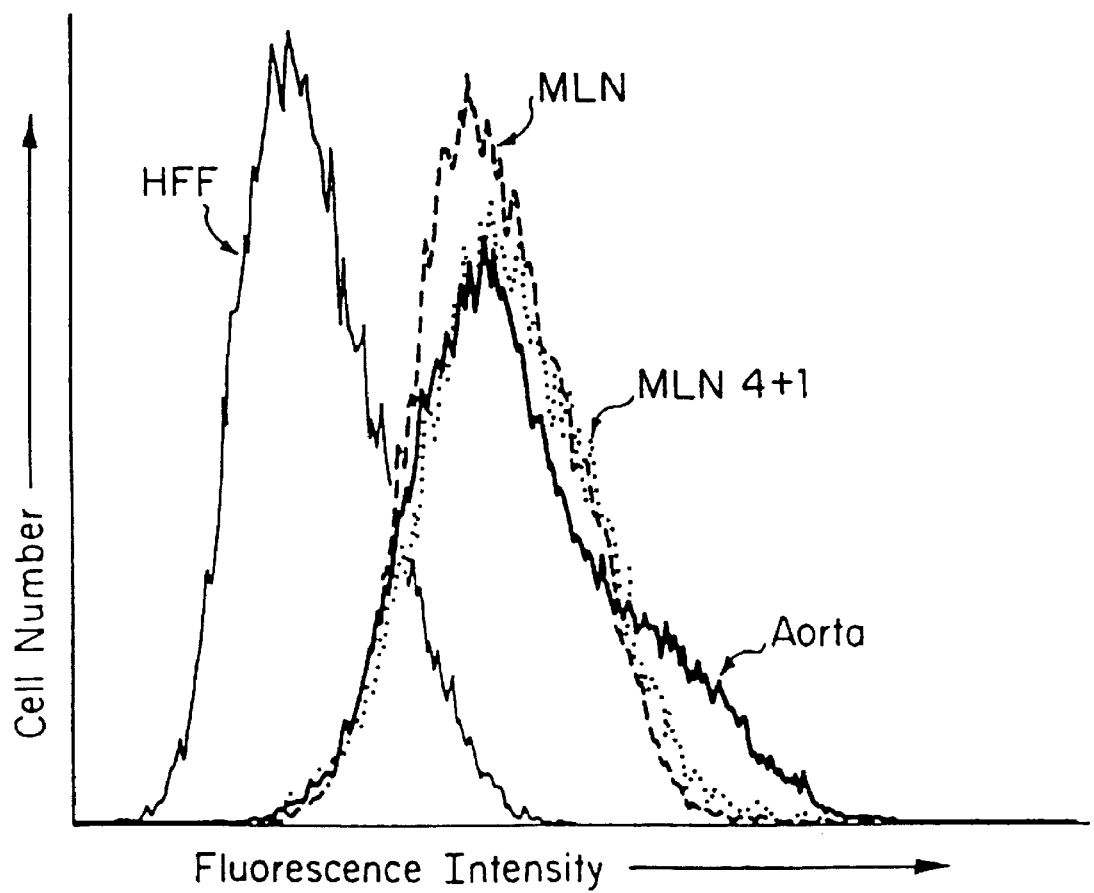
FIG. 2 shows uptake of a representative endothelial-cell marker by cultured microvascular and other endothelial cells, as described in Example 1.

Referring to FIG. 2, uptake of acetylated-LDL, a marker associated with endothelium, by endothelial cells grown in CS-1.55 was similar to that observed for endothelial cells from aorta. In particular, FIG. 2 is a flow cytometric analysis of acetylated-LDL uptake by cultured macaque endothelial cells grown in CS-1.55 from: aorta (heavy continuous line); microvascular endothelial cells of mesenteric lymph nodes (MLN) (dashed line); MLN microvascular endothelial cells activated with IL-4 (10 ng/ml) and IL-1β (1 ng/ml) for 24 hrs (dotted line); and negative-control cultured human foreskin fibroblasts (HFF) (thin continuous line). Cells were exposed to acetylated-LDL (10 μg/ml) for 6 hr, then dislodged with trypsin-EDTA, and analyzed on a Coulter EPICS 720-2 flow cytometer; see Materials and Methods.

Endothelial cells grown in serum-free medium were passaged successfully more than six times without any apparent morphological changes. In contrast, usually after the third passage, microvascular endothelial cells grown in the presence of serum assumed a more flattened shape, frequently losing contacts with the substrate. Accordingly, for serum-containing cultures, only cells from the first two passages were used for adhesion assays.

EXAMPLE 2
Lymphocyte adhesion to cultured cytokine-induced microvascular endothelial cells The capacities of IL-1β, IL-2, IL-4, and IFN-γ to induce endothelium to be more adhesive for lymphocytes was examined as follows. Briefly, cultures of microvascular endothelial cells from macaque mesenteric lymph nodes were cultured in the presence of these cytokines for varying lengths of time, washed, and assayed for lymphocyte adhesion as described below (see Materials and Methods). Monocytes were removed from the lymphocyte suspension prior to assay. The results are shown in Table 1 and FIGS. 3 and 4.

Figures 3A, 3B:
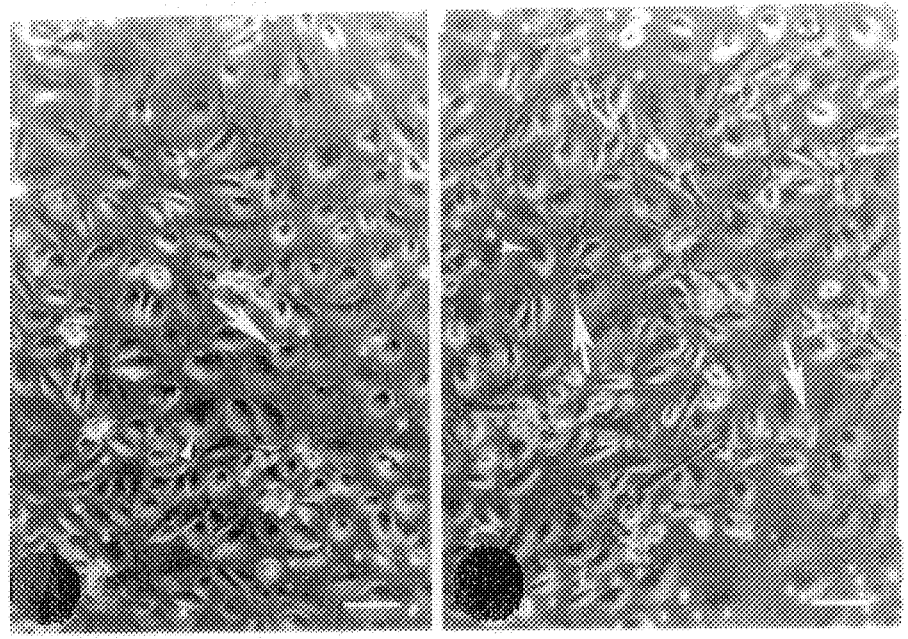
FIG. 3 shows photomicrographs of lymphocyte adhesion to cultured microvascular endothelial cells following cytokine activation, as described in Example 2.
Figures 3C, 3D:
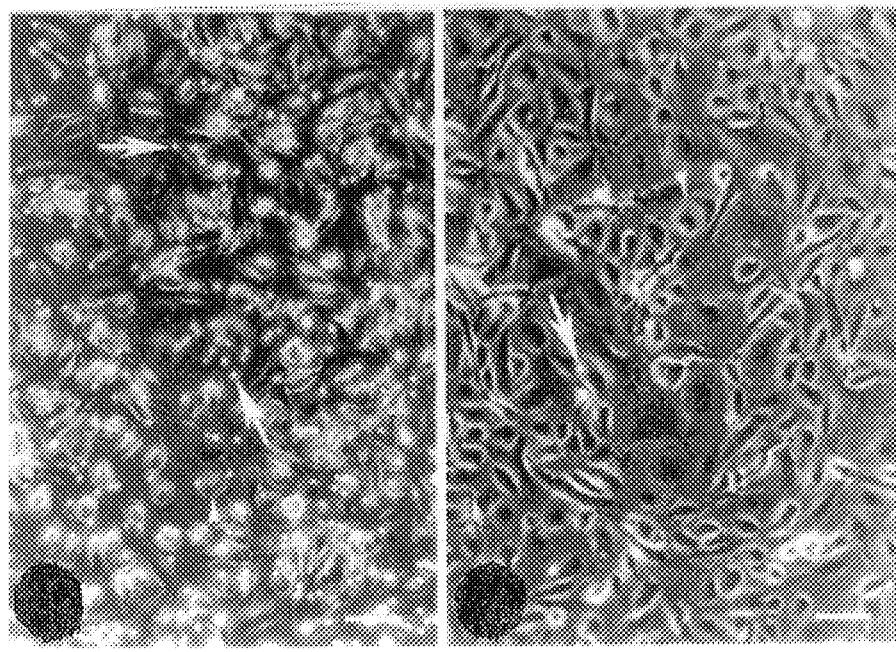

FIG. 3 shows photomicrographs of PBL adhesion to cultured endothelial cells from mesenteric lymph nodes of *Macaca nemestrina*. Endothelial cells were grown to confluency and activated by cytokines for 24 hr. Following the adhesion assay, cells were fixed with 1% glutaraldehyde in PBS. The panels (a–d) indicate endothelial cell activation with: (a) IL-1β (1 ng/ml); (b) IL-4 (10 ng/ml); (c) IL-1β (1 ng/ml) and IL-4 (10 ng/ml); and (d) control, no interleukins added. Arrows indicate adherent lymphocytes; arrowheads, endothelial cells; scale bar, 100 µm.

Figure 4A:
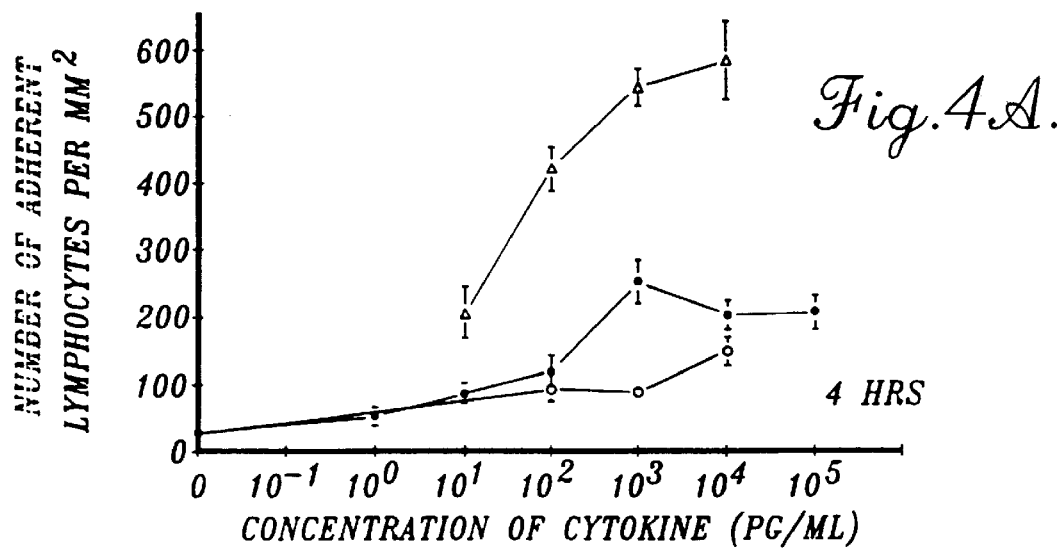
FIG. 4 shows representative time courses of cytokine-induced lymphocyte adhesion to cultured microvascular endothelial cells, as described in Example 2.
Figure 4B:
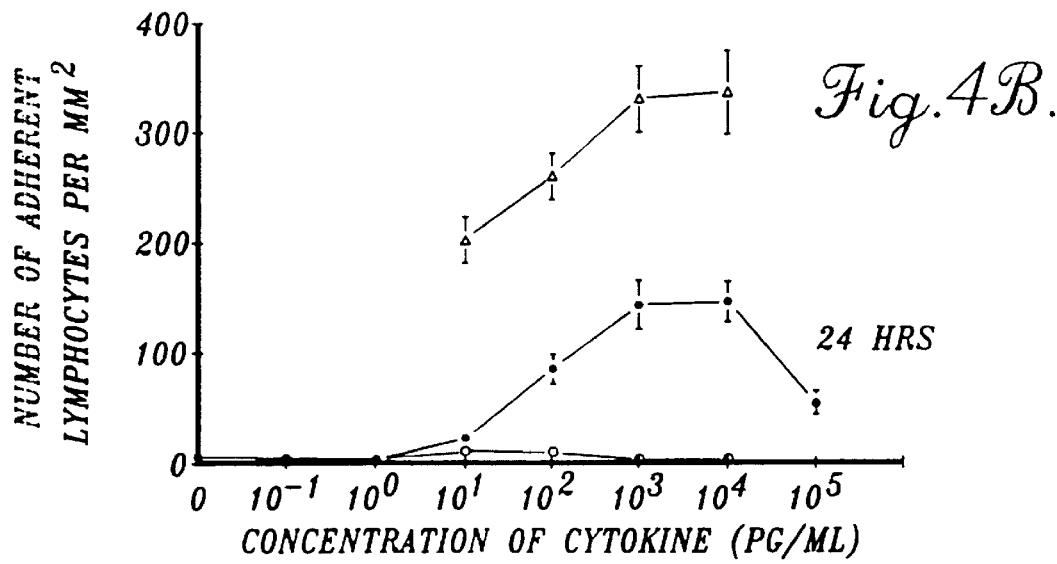
Figure 4C:
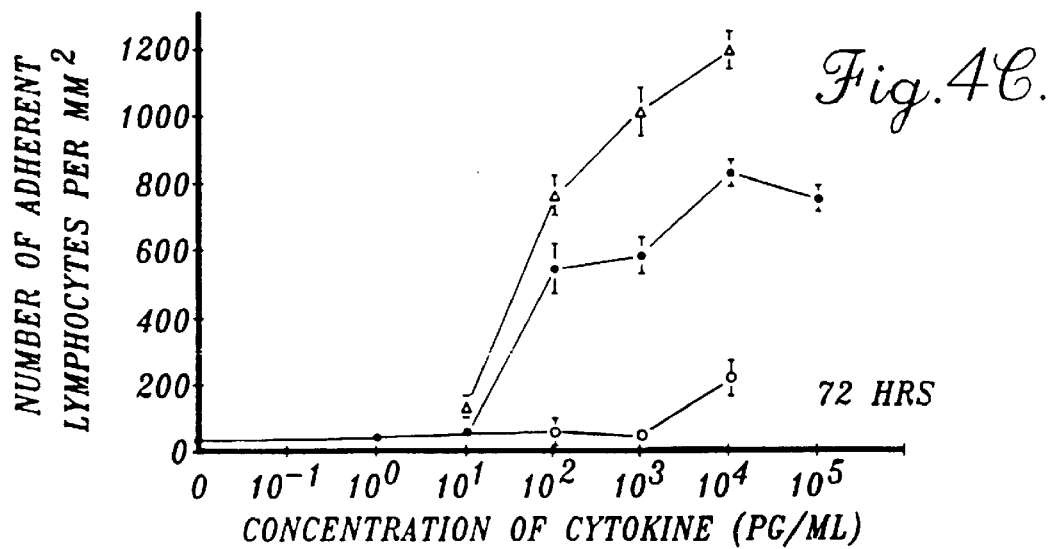

FIG. 4 plots adhesion of PBL to cytokine-activated cultured microvascular endothelial cells at different cytokine concentrations and incubation times. Before each adhesion assay, endothelial cells were treated with cytokines (solid circles, IL-4; open circles, IL-1β; triangles, IL-4in the presence of 1 ng/ml of IL-1β) for the time indicated, which incubation was followed by the adhesion assay. Lymphocyte binding to these endothelial cells was determined by visual count of attached lymphocytes. Each point represents the mean number of attached PBL±SEM.

As anticipated from previous reports (16, 18, 20), after 24 hrs of induction, both IL-1β and IFN-γ treatments yielded similar increases in the number of adherent lymphocytes. Stimulation indices of 2 to 4 compared to controls were typical for cytokine concentrations in the range of 1 pg/ml to 10 ng/ml (FIG. 3 and Table 1). IL-2 had no effect on lymphocyte binding at any concentration tested (Table 1, and data not shown).

In contrast to the rather minimal effects observed with the other cytokines, IL-4 treatment consistently yielded the most dramatic increase in lymphocyte adhesion (FIGS. 3 and 4, and Table 1). The level of PBL adhesion to IL4-induced endothelial cells exceeded that of the control (no cytokines) by up to 45-fold (FIG. 4, 24 hr). The optimum concentration of IL-4 that promoted abundant adhesion of lymphocytes to endothelial cells was in the range of 100 pg/ml to 10 ng/ml; this optimum was common for all time periods (4, 24, and 72 hrs) of endothelial cell exposure to this cytokine (FIGS. 3 and 4). At these concentrations, the absolute numbers of lymphocytes bound to IL4-exposed endothelial cells were consistently in the range of 200–1300 lymphocytes/mm², while on the control endothelial cells only 5–40 lymphocytes/mm² were observed. The stimulation index (which ranged from 2 to 45) varied among different animals used as a source for microvascular endothelium, and was lower for endothelial cells propagated in serum-free medium, due essentially to the higher background adhesion on endothelial cells cultured in this manner (Table 1).

IL-4 promoted adhesion by acting on microvascular endothelial cells rather than on lymphocytes, since addition of an anti-IL-4 antibody to the cultures during the assay, or addition of IL-4 to lymphocyte suspensions for 30 min prior to assay, did not affect the lymphocyte binding to cultured endothelial cells. IL4-induced adhesion was detected as early as 4 hr after cytokine treatment, plateaued by 12–2 hr, and remained in evidence through at least 72 hr in the continued presence of IL-4 (FIG. 4). The effect of IL-4 was relatively specific to cultured microvascular endothelial cells, since addition of this cytokine to other adherent cells, such as fibroblasts, which have functional receptors for IL-4 (41–44), did not result in increased lymphocyte adhesion in our system (data not shown). At the highest tested concentrations of IL-4 (50–100 ng/ml) and of IL-1β (5–10 ng/ml), cultured microvascular endothelial cells underwent morphological changes, converting from a cobblestone phenotype to a more flattened appearance with fewer cell-cell contacts and a detachment of cells from the plates. These changes were apparent after 24 hrs of cytokine exposure and resulted in decreased lymphocyte adhesion per unit area of the culture well.

EXAMPLE 3

Synergism between IL-4 and IL-1 in promoting lymphocyte adhesion to cultured microvascular endothelial cells Because IFN-γ, IL-1β, and IL-4 all enhanced adhesion to microvascular endothelial cells, and since these cytokines had been reported to synergize with other interleukins in promoting various hemopoeitic activities (45, 46), we tested their effect on microvascular endothelial cells in combination. After 24 hours of costimulation the effects of IL-4 and IFN-γ were at best additive with no significant synergy in evidence (Table 1). Similarly, additive but not synergistic activity was observed when IL-1β and IFN-γ were applied in conjunction (data not shown). In contrast, the amount of lymphocyte adhesion observed when both IL-4 and IL-1β were added to the microvascular endothelial cell cultures was markedly increased over that expected from purely additive effects (FIGS. 3 and 4, Table 1). When the amount of IL-1β was held constant (0.1 or 1 ng/ml) and varying amounts of IL-4 were added, synergistic activation of cultured endothelial cells was observed over a wide range of cytokine concentrations (FIG. 4). In the presence of as little as 1 pg/ml of IL-4, addition of IL-1β increased lymphocyte adhesion 2.5 to 7 times compared to that detected with IL-4 alone (FIG. 4). For lower concentrations of IL-1β (0.1 ng/ml), synergistic lymphocyte adhesion was approximately half of that observed at 1 ng/ml. Addition of IL-1β did not significantly alter the kinetics of the response to IL-4, nor did it change the optimum concentrations of IL-4 that promoted adhesion (FIG. 4). The super-additive effect of IL-1β and IL-4 was manifest only under certain culture conditions. For endothelial cells grown in serum-free medium, CS-1.55, which typically had background adhesion 5–10 fold higher than that observed in other media, the effects of these two cytokines were only additive (Table 1).

Figure 5:
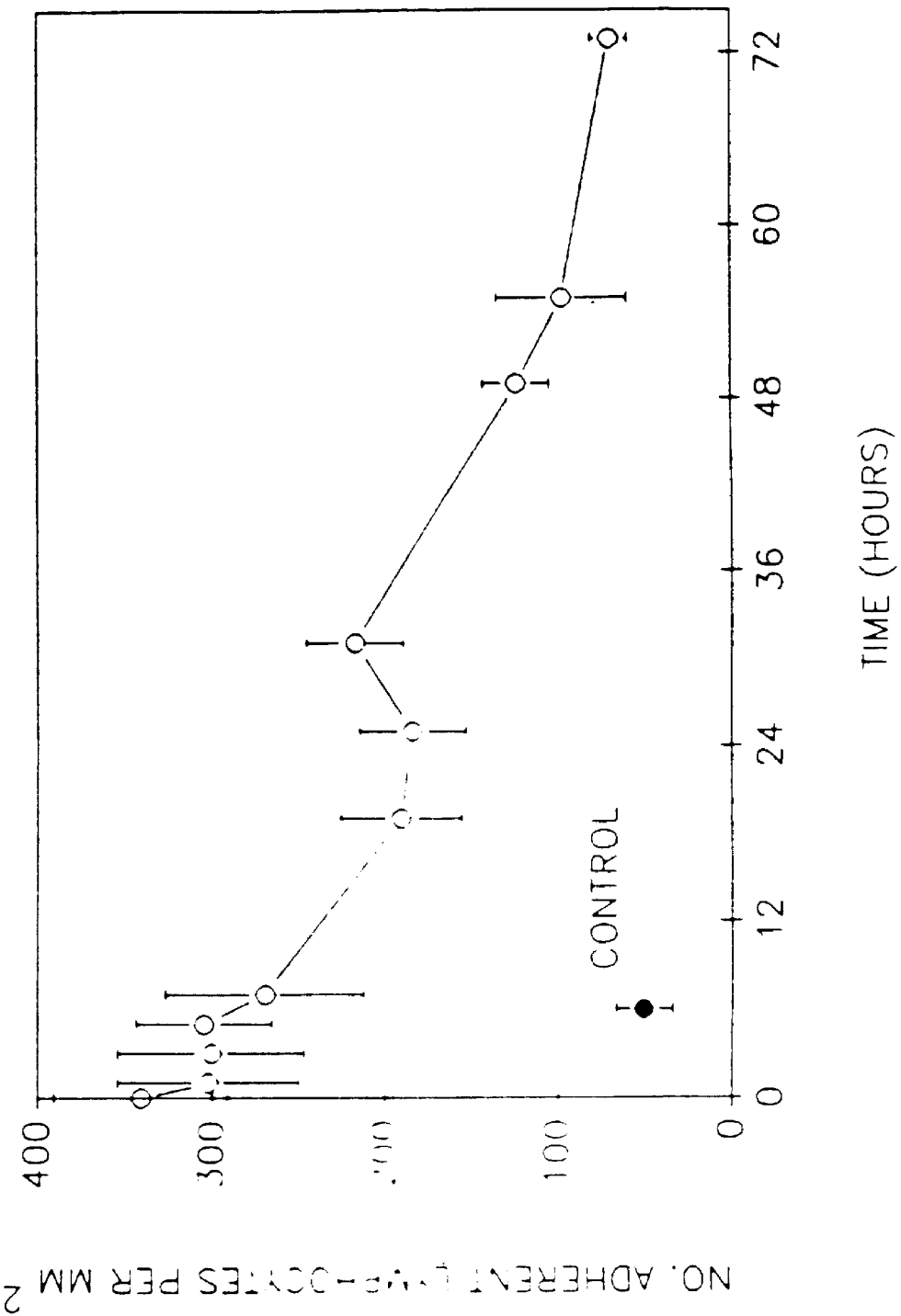
FIG. 5 shows stability of IL4/IL-induced lymphocyte adhesion to endothelial cells, as described in Example 3.

Referring to FIG. 5 in more detail, after 24 hr incubation with IL-4 (1 ng/ml) and IL-1β (1 ng/ml), the cytokines were removed. The adhesion assay was conducted after additional incubation without any lymphokines. Each point (open circles) represents the mean adherence±SEM of eight readings. Control endothelial cells (solid circle) received no cytokine added.

The combinatorial effect of IL-1β and IL-4 on lymphocyte binding to microvascular endothelial cells required de novo protein synthesis. If after 2 hr of cytokine activation with IL-1β (1 ng/ml) and IL-4 (10 ng/ml), the metabolic inhibitor, emetine, was added, adhesion observed 2 hr later was inhibited to 10% of that seen without addition of emetine. In similar experiments, if emetine was added after 70 hr of endothelial cell activation, adhesion measured at 72 hr was unaffected compared to controls. Once induced, the adhesive function of endothelial cells was relatively stable over time. Maintenance of the relevant cell adhesion molecules in a functional form did depend, however, on continued presence of the cytokines. When endothelial cells were incubated with IL-1β and IL-4 for 24 hr, and then the interleukins were removed, the capacity to support lymphocyte adhesion was almost unchanged during the first 8 hr, decayed by 50% at 24 hr, and returned to essentially background levels by 72 hr (FIG. 5).

EXAMPLE 4

Figure 6:
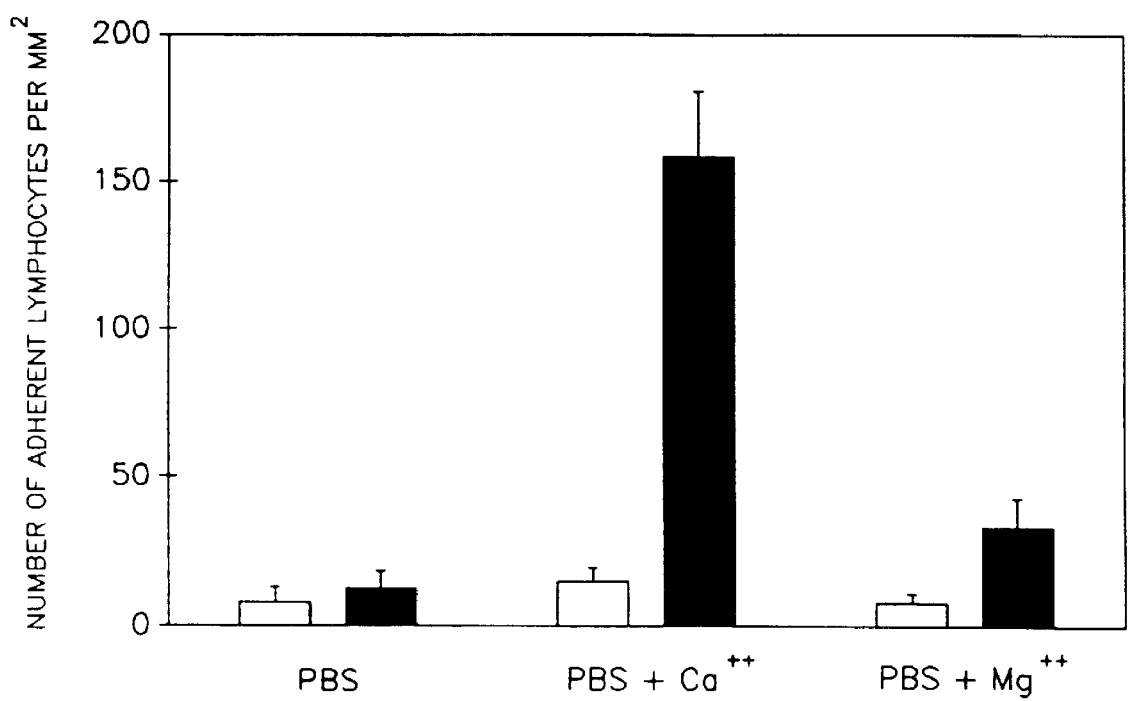
FIG. 6 shows lymphocyte adhesion to IL4/IL1-activated endothelial cells is divalent cation dependent, as described in Example 4.
Figure 7A:
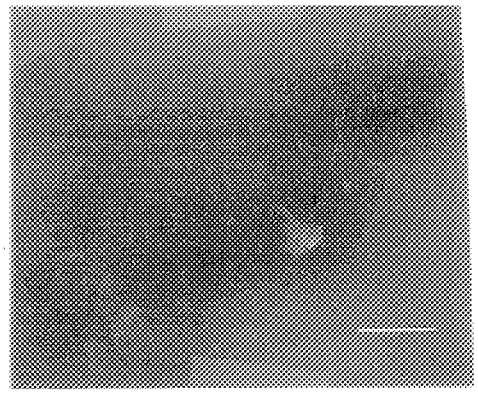
FIG. 7 shows labeling of cultured microvascular endothelial cells with mAb 6G10, as described in Example 4.
Figure 7B:
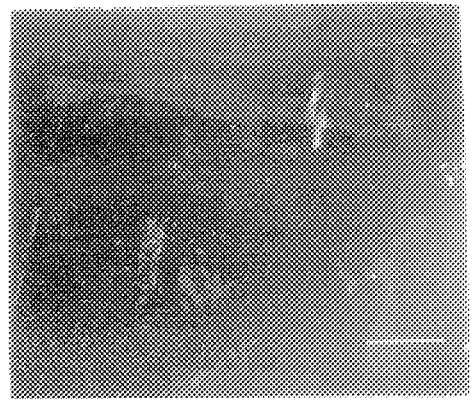
Figure 7C:
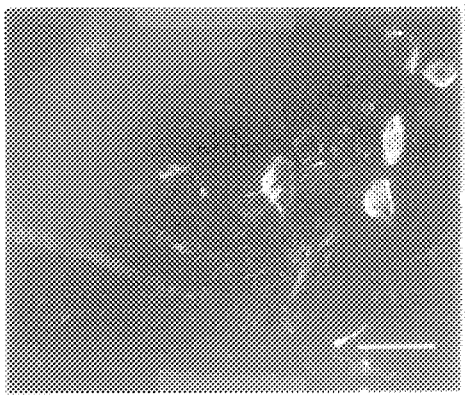
Figure 7D:

Identification of one CAM involved in IL-4 induced lymphocyte adhesion to microvascular endothelial cells A priori, IL-4's effects in this system could be manifest through induction of known adhesion molecules, or might involve expression of novel CAMs. To examine these possibilities, the following approaches were taken. First, the temperature dependence and cation requirements of lymphocyte binding were determined. Temperature dependence was minor, with robust adhesion observed at both 4° and 37° C. (FIGS. 3 and 4, Table 1, and data not shown). Also, lymphocyte binding was divalent cation dependent, with a primary requirement for calcium rather than magnesium ions (FIG. 6). Both of these facts tend to exclude LFA-1 (CD11/CD18)/ICAM-1 mediated interactions since these are sensitive to low temperature and utilize magnesium as the preferred cation (47).

Referring to FIG. 6 in detail, endothelial cells were activated with IL-1β (1 ng/ml) and IL-4 (10 ng/ml) for 24 hr. Subsequently, endothelial cells were fixed in 1% paraformaldehyde in PBS, washed, and the adhesion assay was conducted in PBS-based medium containing 1% BSA and 1% glucose to which $Ca^{++}$ or $Mg^{++}$ were added as shown. Each bar represents the mean number of adherent lymphocytes±SEM of four readings. Closed bars: IL1/IL4-activated endothelial cells; open bars: control, no cytokine added.

Secondly, the sensitivity of IL-4 induced adhesion to blockade by mAb known to interfere with cell-cell interactions mediated by the CAMs, CD44, MECA-79, and by interactions between LFA-1 and ICAM-1 was tested by pretreating the relevant cell (i.e., lymphocyte or endothelial cell) with each mAb prior to assay (see Materials and Methods). Although all these reagents reacted well with macaque endothelial cells and/or lymphocytes in culture or in tissue sections, none of them interfered significantly with lymphocyte binding under these conditions. Since upregulation of class II MHC molecules on endothelium had been reported after induction with IFN-γ and TNF-α (50–52), an anti-class II MHC mAb, Hb10a, was also tested and likewise did not effect lymphocyte attachment (data not shown). A similar assessment could not be made for ELAM-1 since the available antibodies against this molecule did not react well with macaque endothelial cells. Nonetheless, other differences between ELAM-1 mediated adhesion and that observed following IL-4 stimulation were inconsistent with involvement of this particular CAM in a primary role (see above). In parallel experiments conducted with two different antibodies (4B9 and E1/6) against human VCAM-1 (aka INCAM-110 (28–30)), only weak reactivity with cytokine-induced microvascular endothelial cells was detected by immunofluorescent confocal microscopy (data not shown). However, in one experiment out of four conducted, an inhibition (40%) of lymphocyte binding to IL4/IL1-induced microvascular endothelial cells was detected. Although inconclusive, this result suggested that VCAM-1 might contribute to the process of attachment, especially since mAb's 4B9 and E1/6 were relatively species specific. These mAb's reacted poorly in immunocytochemical tests of macaque tissues.

Figure 8:
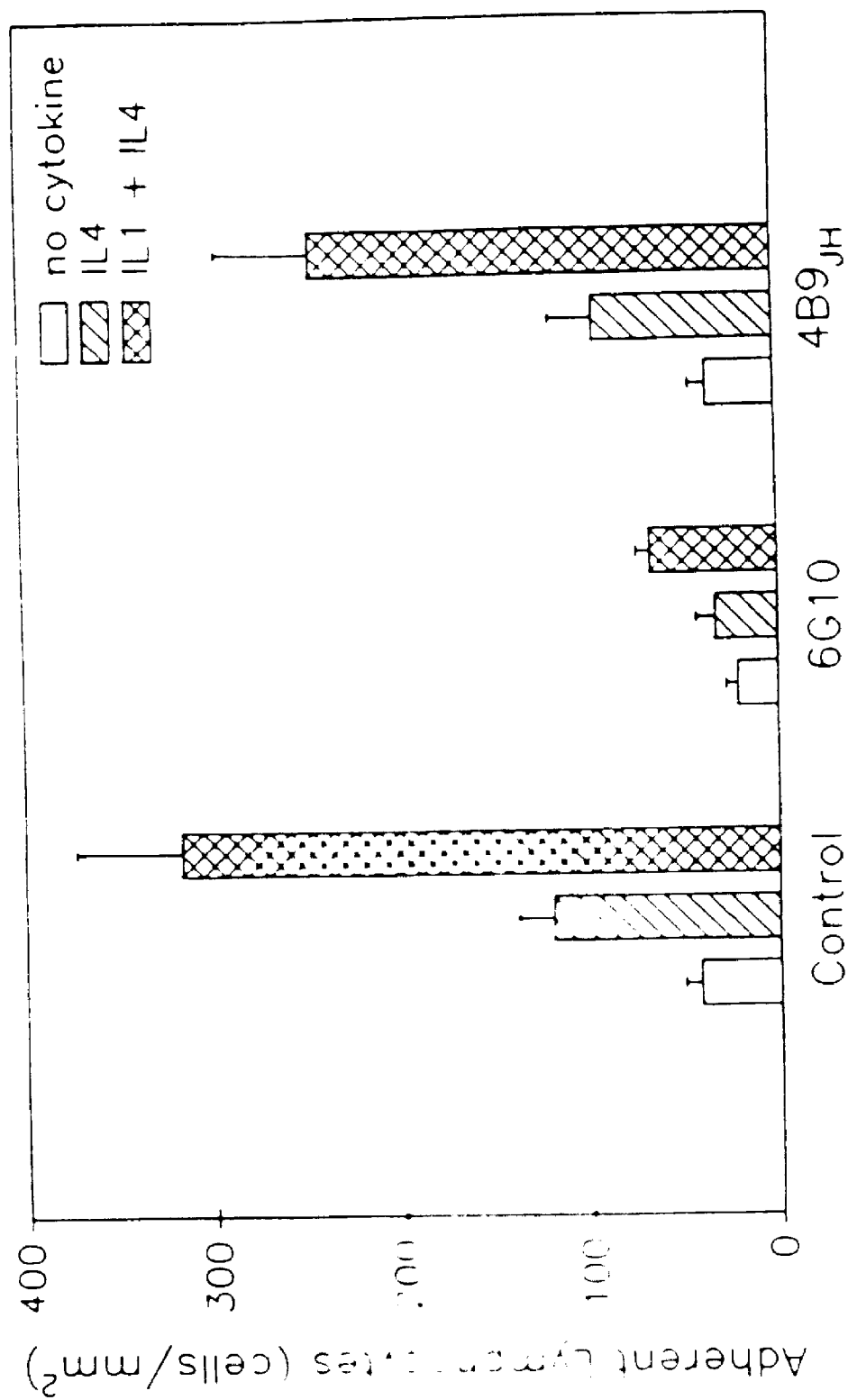
FIG. 8 shows monoclonal antibody 6G10 blocks the lymphocyte adhesion to IL4/IL1-induced macaque microvascular endothelium, as described in Example 4.
Figure 9A:
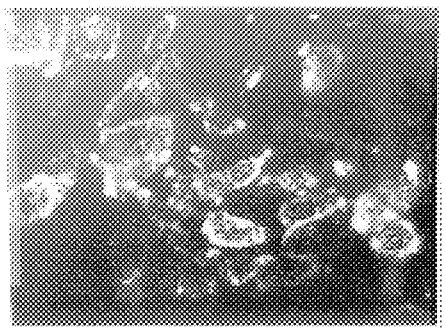
FIG. 9 shows labeling of CHO transfected cells with mAb's 6G10 and 4B9, as described in Example 4.
Figure 9B:
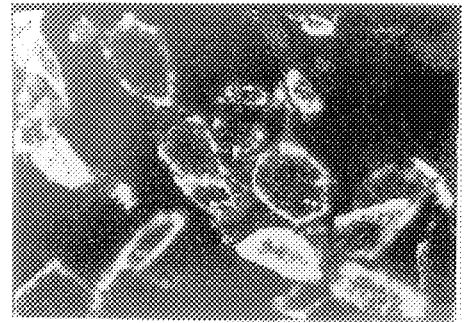
Figure 9C:
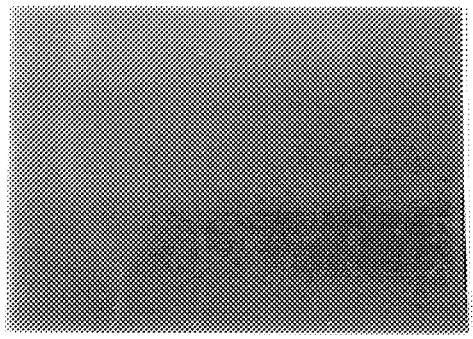
Figure 9D:
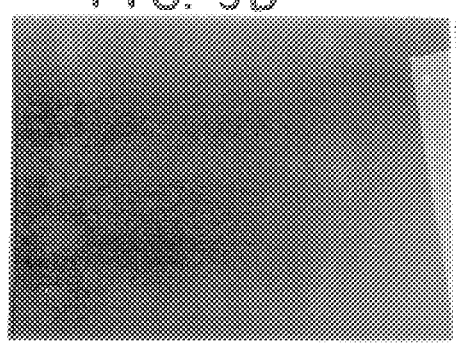

To resolve the issue, mAb's specific to IL-4 induced macaque endothelial cells were prepared (see Materials and Methods). Briefly, hybridomas derived from fusions using spleen cells from mice immunized with cytokine-stimulated endothelial cells were first screened by ELISA for selective reactivity with IL4/IL1-activated endothelium. Positive clones were tested secondarily for their ability to block lymphocyte binding to endothelial cells under various conditions of cytokine treatment. One mAb elicited in this manner, 6G10, detected on cultured endothelial cells a cell-surface antigen whose expression paralleled the amount of lymphocyte adhesion induced by each cytokine (i.e., IL1β+IL-4>IL-4>IL-1β, FIG. 7). More importantly, 6G10 blocked up to 80% of lymphocyte adhesion occurring after endothelial cell treatment with IL-1β/IL-4 (FIG. 8). To clarify the identity of the structure recognized by mAb 6G10, this reagent was tested by indirect immunofluorescence for reactivity with CHO cells transfected with cDNAs encoding human ELAM-1, ICAM-1, VCAM-1, or CD4 as a control. We found that mAb 6G10, similar to mAb 4B9, bound specifically with transfectants expressing the product of the VCAM-1 gene (FIG. 9). No reactivity was observed on the other transfectants. By extension then, lymphocyte binding to IL-4 stimulated endothelial cells in this system most probably utilizes the macaque homologue of human VCAM-1 or a serologically related molecule as a major adhesive component.

Referring to FIG. 7 in detail, endothelial cells were activated for 24 hr with: panel A, control, no cytokine added; panel B, IL-1β (1 ng/ml); panel C, IL-4 (10 ng/ml); and panel D, IL-4 (10 ng/ml) and IL-1β (1 ng/ml). After stimulation, unfixed cells were exposed to mAb 6G10 for 2 hr at room temperature, which was followed by exposure to biotinylated secondary antibody, avidin-FITC labeling, and analysis on Bio-Rad laser scanning confocal microscope. Note an increase of immunofluorescence with IL-4 and IL-1β+IL-4 activation of endothelial cells. Scale bar is 50 μm.

Referring to FIG. 8, endothelial cells were activated with IL-4 (10 ng/ml) alone or in a combination with IL-1β (1 ng/ml) for 24 hr. After removal of cytokines, cells were exposed to either mAb 4B9 or 6G10 for 30 min, and the adhesion assay was conducted. Each bar represents mean number of adherent lymphocytes±SEM of four readings.

FIG. 9 shows immunofluorescence of: panel A, human VCAM-1 transfectant labeled with 6G10; panel B, same as in (A) but labeled with 4B9; panel C, human ICAM-1 transfectant labeled with 6G10; and panel D, human ELAM-1 transfectant labeled with 6G10. Scale bar is 100 μm.

Figure 10:
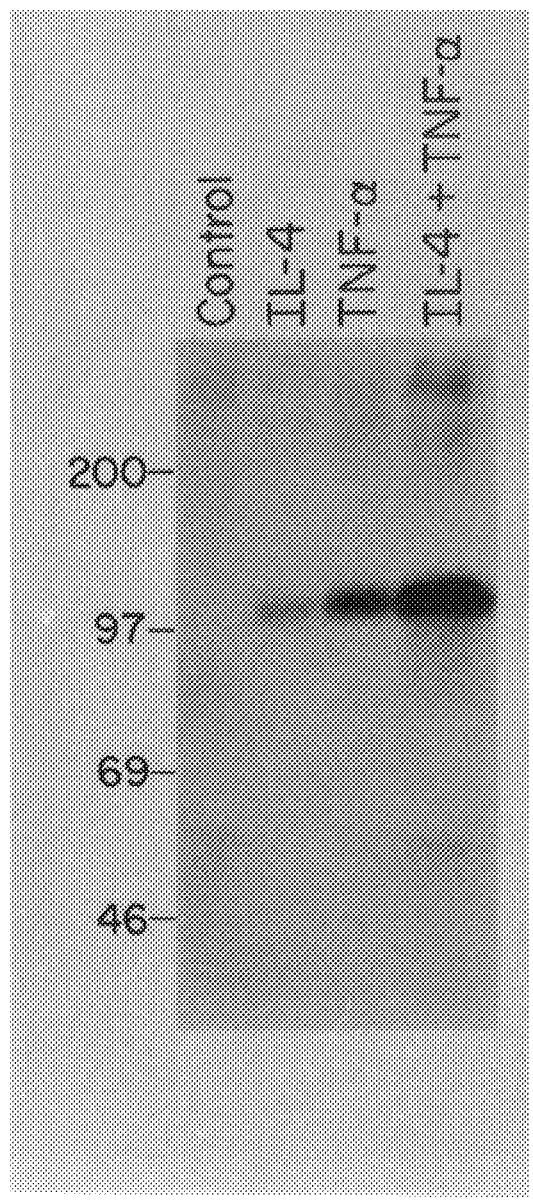
FIG. 10 shows that mAb 6G10 recognizes an approximately 110 kD molecule on cytokine-activated endothelial cells, as described in Example 4.

FIG. 10 shows radioimmunoprecipitation of cell surface molecules of microvascular EC with mAb 6G10. EC were grown to confluency in complete EBM and were either activated with IL-4 (10 ng/ml), TNF-α (10 ng/ml), or IL-4 (10 ng/ml) and TNF-α (10 ng/ml), or served as a control receiving no cytokines. EC were labeled with $^{125}I$, lysed, immunoprecipitated with mAB 6G10, and electrophoresed on a 10% SDS gel under reducing conditions. Note distinct band at 110 kD at lanes 2–4, which is absent in the control lane.

EXAMPLE 5

IL-4 and TNF induce mAb 6G10-recognized expression on bone marrow stromal cells

Thirteen years ago, Dr. Michael Dexter and his colleagues (65) established the methodology for maintaining the survival and development of primitive bone marrow stem cells over long periods of time in vitro. This so-called long-term bone marrow culture (LTBMC) system, while initially optimized for the growth of murine cells, has subsequently been modified to support the growth of human bone marrow (66). The essential feature of both systems is the development of an adherent layer of mesenchymal cells derived from the stromal cell population of the bone marrow. The inductive influences provided by the stromal elements of these cultures are essential for the growth and self-renewal and the differentiation of stem cells in these cultures to more specialized progeny (e.g., myeloid progenitors) in a manner which reflects the in vivo situation. Both cytokines released by the stromal cells and adhesive interactions between stromal cells and hemopoietic precursors are important in this process (67, 68). At this point, many of the specific adhesive mechanisms utilized in this in vitro system and its in vivo counterpart are ill-defined.

Figure 11A:
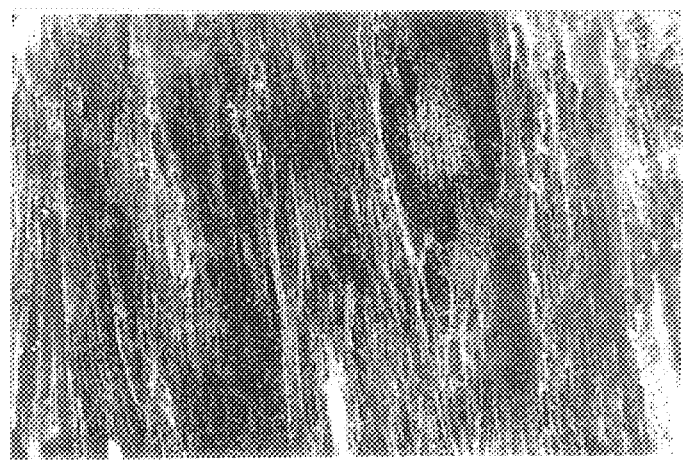
FIG. 11 shows IL4/TNFα-enhancement of mAb 6G10-recognized antigen expression on bone marrow stromal cells, or described in Example 5; and, FIG. 12 shows that the VLA-4 receptor for VCAM-1 is expressed at high levels on bone marrow cells bearing the CD34 antigen, as described in Example 5.
Figure 11B:
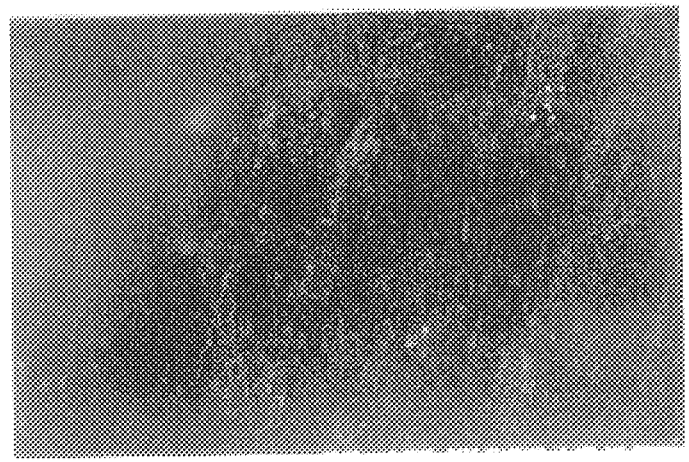

We have discovered that the antigen recognized by mAb 6G10 is expressed on human bone marrow stromal cells in vitro especially after induction with IL-4 and/or TNF. FIG. 11 shows human bone marrow stromal cells grown in long-term marrow culture according to established methods for 2 weeks. In this representative experiment, the cultures were treated for 25 hr with recombinant human TNF-α and IL-4 (10 ng/ml) prior to immunolabeling with mAb 6G10 (20 μg/ml) (panel A), or isotype-matched control antibody (panel B) and goat antimouse IgG-FITC (Southern Biotechnology Assoc.). Immunofluorescence images were recorded using a scanning laser confocal microscope. The IL4/TNFα-enhancement of 6G10-recognized antigen expression on the stromal cells is evident in panel A. This novel finding would not have been predicted a priori from available information about the tissue distribution of VCAM-1. Interestingly, mAb 4B9 (from John Harlan), which also recognizes VCAM-1 on human endothelium, did not bind significantly to human bone marrow stroma cultured in this manner. Therefore, the antigenic epitope recognized by mAb 6G10 may be unique compared to that bound by mAb 4B9. Cell-surface molecules immunoprecipitated with mAb 6G10 from TNFα/IL4-activated cultured human bone marrow stroma differed from that observed on activated omentum EC. The 6G10-recognized molecules were larger in size—one of the species having a molecular weight of 115–130 kD, while the other was larger than 200 kD—as compared to the 100 kD of traditional VCAM-1.

Figure 12:
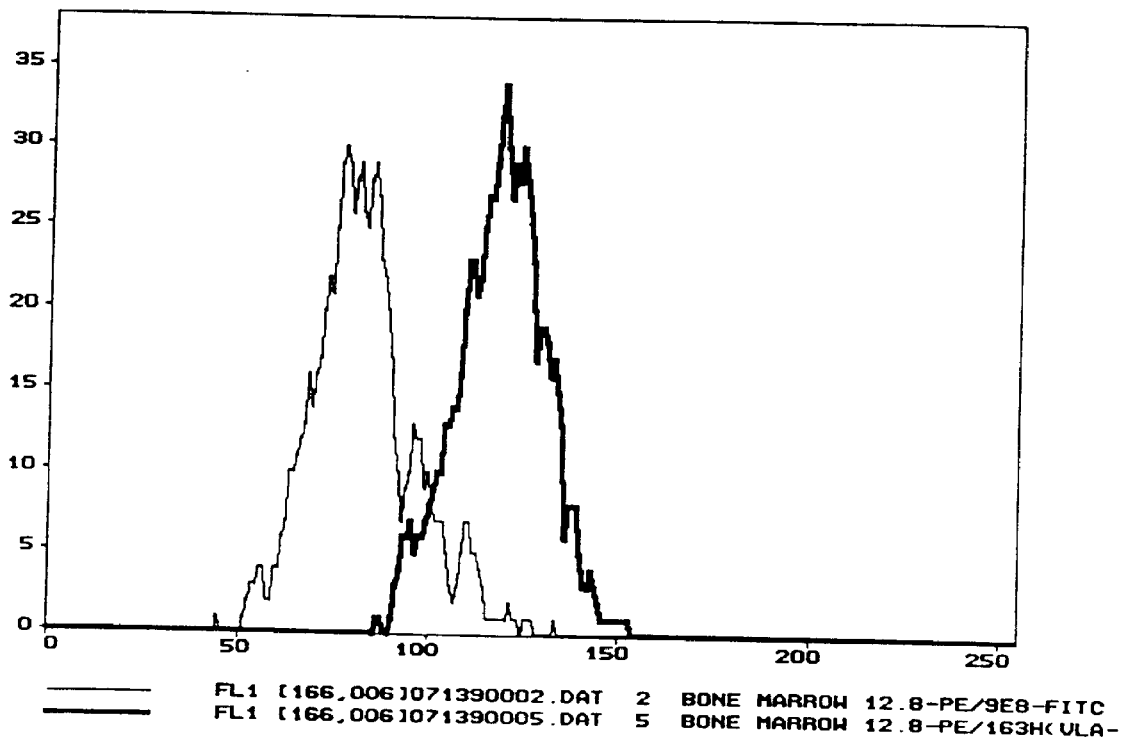

Further, we have discovered that a major receptor for VCAM-1, VLA-4 (also known as integrin alpha4/beta1 (69)), is expressed at high levels on bone marrow cells bearing the CD34 antigen. FIG. 12 shows confirming FACS plots of human CD34$^+$ bone marrow cells stained with negative control mAb (thin line), and anti-VLA-4 mAb 163H (thick line). This finding of coexpression is significant because CD34 expression distinguishes a subset of bone marrow cells (1–4%) which are enriched in primitive stem cells and progenitors (70). Therefore, we infer that adhesive interactions within the bone marrow between hemopoietic stem cells and/or progenitor cells and stromal cells may be mediated by the binding of VLA-4 and the antigen recognized by 6G10. It has been demonstrated in a large animal system (canine) and in man that antibodies directed against two known adhesion molecules, CD44 and LFA-1, respectively (71, 72, 73), administered before or during bone marrow transplantation facilitate the transplantation process in cases where the grafted marrow and recipient are not perfect genetic matches.

It follows that mAb 6G10 and its antigen-binding derivatives, as well as other hybridoma-generated or recombinantly engineered binding partners having antigen-binding specificities like mAb 6G10, VCAM-1 and its derivatives, particularly those recognized by mAb 6G10, and VLA-4 and its derivatives are useful either in vitro or in vivo to modify in either a positive or negative fashion the growth or differentiation of bone marrow stem cells or bone marrow stroma. For example, the disclosed cytokines and reagents are useful to facilitate the success of bone marrow transplantation, either by enhancing the growth of the graft (e.g., by IL-4 or TNF-α administration), or by preventing graft versus host disease (e.g., by pretreatment with soluble VCAM-1 receptor recognized by mAb 6G10, or antibodies directed to the VLA-4 receptor recognized by the antigen recognized by mAb 6G10).

The disclosed reagents can also be used to immunoselect (e.g., by FACS cell sorting, magnetic bead selection, or negatively by complement lysis) primitive hemopoietic stem cells, progenitor cells, or bone marrow stromal elements.

The above-stated applications are particularly useful in cases where the disclosed cytokines are administered either in vivo or in vitro to promote bone marrow transplantation as a curative regimen for neoplastic disease or anemia.

The disclosed reagents are readily conjugated to radionuclides or other pharmaceutical moieties to provide targeting devices to achieve high specific localization of the radionuclides or pharmaceutical agents to the bone marrow, for purposes of radioimaging or therapy of neoplastic disease, anemia, or benign hyperplasias of hemopoietic origin.

Since IL-4 and TNF-α induce 6G10 antigen expression on bone marrow stroma, the coordinated use of either cytokine in vivo with injection of the aforementioned antibody or receptor conjugates can achieve enhanced specificity of antibody or receptor conjugate localization to the bone marrow.

Materials and Methods

Endothelial cell cultures. Mesenteric lymph nodes of 0.5- to 7-year-old *Macaca nemestrina* were obtained through the Tissue Distribution Program of the Regional Primate Research Center at the University of Washington, Seattle, Wash. The lymph nodes were transported in an ice-cold washing solution composed of RPMI-1640 medium buffered with 25 mM HEPES, pH 7.0, and containing tylosin and gentamycin (Sigma). For separation of small blood vessels and endothelial cells, a modification of the method described by Williams (35) was used. Briefly, lymph nodes were cut into pieces and transferred to a digestive solution containing 0.5 mg/ml collagenase Type IV (Sigma), 0.5 mg/ml dispase (Boehringer-Mannheim), and 0.05 mg/ml DNAse (Boehringer-Mannheim) in complete Waymouth medium (WM), pH 7.2, containing 10% heat inactivated fetal bovine serum (FBS, HyClone) and penicillin/streptomycin (GIBCO). The tissue was incubated at 37° C. and agitated by vortexing every 15–20 minutes. Collections of suspended, single cells and small cell aggregates were performed every 0.5–1 hr. Small clumps of cells, fragments of capillaries and larger vessels were separated from the majority of lymphocytes and individual stromal cells by brief centrifugation at 200×G. Pellets were washed in the washing solution and resuspended in either complete WM, or in complete Endothelial Basal Medium (EBM, Clonetics) with 2% FBS, or in serum-free endothelial cell medium CS-1.55 (Cell Systems) with endothelial cell growth supplement (ECGS, 10 μg/ml, Cell Systems) and heparin (50 μg/ml, Cell Systems). Cells were cultured at 370° C. with 5% $CO_2$ in 25 cm$^2$ flasks (Falcon) coated previously with 1% gelatin (Sigma) in phosphate buffered saline (PBS), pH 7.0. Approximately 18 hr later, unattached cells were aspirated with fresh medium added. Growing fibroblasts were removed either mechanically with a scraper, or by a 90 sec digestion with 1× trypsin/EDTA (Gibco) on day 5–10. This procedure was repeated every 3–7 days. When endothelial cells grew to confluence, cells were dislodged by a treatment with 1× trypsin/EDTA and passaged at a 1:3 ratio into new flasks. Only cultures in which at least 95% of cells had morphology and markers characteristic of endothelial cells (e.g., uptake of acetylated low density lipoprotein, lack of cytokeratin expression) were used for subsequent experiments. Under these conditions, cells having morphological and immunohistological markers characteristic of monocytic or dendritic cells were rarely seen in the cultures.

For adhesion assays, cells from the first two passages were plated at 5×10$^3$/well on gelatin-coated 24-well plates (Costar) or uncoated 24-well Primaria™ plates (Falcon) and incubated until they reached confluency, usually for one week. After removing spent medium, 1 ml/well of fresh medium alone or containing a cytokine, either human recombinant IL-1β, IL-2, IL-4 (Immunex), or IFN-γ (Alpha Therapeutic), or a combination of these was added, and cells were grown for an additional 4–72 hrs. Other sources of human recombinant IL-4 and IL-1β include Research & Diagnostic Systems, Minneapolis, Minn. In experiments to test dependency on protein synthesis, emetine (Sigma) was added at a final concentration of 50 μM prior to the adhesion assay.

Low density lipoprotein (LDL) uptake. Cells were incubated with acetylated low density lipoprotein labeled with dioctadecyltetramethylindocarbocyanine perchlorate (DiI-Ac-LDL, Biomedical Technologies) at 10 μg/ml for 4 hrs at 37° C. Following 2 washes with PBS, cells were dislodged with trypsin-EDTA, fixed with 2% paraformaldehyde in PBS, and analyzed using 555 nm excitation on a Coulter EPICS 750-2 flow cytometer. A total of $2 \times 10^4$ events were collected as list mode files and reprocessed using Reproman™ software (TrueFACS) using forward-angle light scatter to exclude dead cells. Endothelial cells from macaque aorta grown in complete CS-1.55, and human foreskin fibroblasts (a gift from T. Brown, FHCRC), served as positive and negative controls, respectively.

Adhesion assays. Peripheral blood lymphocytes (PBL) of *Macaca nemestrina* were separated from other blood elements by centrifugation on a discontinuous Ficoll gradient as described previously (39). To remove macrophages and other highly adherent leukocytes, cells were incubated in complete WM at $3 \times 10^6$ cell/ml on regular tissue culture Petri dishes (Falcon) for 1–2 hrs at 37° C. For adhesion assays, endothelial cells on 24-well plates were washed twice with ice-cold adhesion buffer (HEPES buffered RPMI-1640, pH 6.8, with 1% FBS and 1% glucose); 0.4 ml of adhesion buffer was aliquoted per well; and plates were placed on a gyratory shaker (New Brunswick) at 50 rpm at 4° C. Lymphocytes were collected from Petri dishes, counted, resuspended in ice-cold adhesion buffer at $2.5 \times 10^6$ cell/ml, and added to endothelial cell monolayers (0.2 ml/well). After 30 min, cells were fixed by gentle addition of 2% glutaraldehyde in PBS to each well. After two washes with PBS, lymphocyte adhesion was quantified by light microscopy according to the following procedure. For enumeration, each well was divided into four equivalent sectors. Within each sector the number of lymphocytes adhering to endothelial cells was determined for a microscopic field corresponding to 0.24 mm² of the well. Results are expressed as a mean±standard deviation. In experiments to test divalent cation dependence, endothelial cells were paraformaldehyde-fixed prior to assay, washed in PBS; and the assays were carried out in PBS with 1% bovine serum albumin, 1% glucose, with and without the addition of $Ca^{++}$ (1 mM) or $Mg^{++}$ (1 mM).

Production of mAb against cytokine-induced endothelial cells. For immunizations of Balb/c mice (Jackson Laboratories), cultured microvascular endothelial cells were activated with IL-4 (10 ng/ml) and IL-1β (1 ng/ml) for 24 hrs, washed with PBS, and dislodged with a scraper. After centrifugation at 200×G, the pellet was resuspended in PBS (0.5 ml/mouse) containing adjuvant peptide, muramyl dipeptide (50 μg/mouse, Sigma), and cells ($1–5 \times 10^6$/mouse) were injected into mice subcutaneously (neck region) and intraperitoneally. Four subsequent boasts were conducted over a period of 8 months. Four days after the last boost, the spleen was removed, and lymphocytes were fused with NS-1 myeloma cells using polyethylene glycol (MW-1500, Aldrich) as described by Kennett (40). Selection of hybridomas was accomplished with aminopterin (Sigma). ELISA screening of supernatants was conducted on IL4/IL1-activated versus nonactivated microvascular endothelial cells, after which positive clones were tested in the adhesion assay for their ability to block lymphocyte binding to cytokine-activated endothelial cells. Selected hybridomas were subcloned at least three times. For the production of pure monoclonal antibodies (mAb's), hybridomas were grown in serum-free medium (Nutridoma-NS, Boehringer-Mannheim) and immunoglobulin was precipitated with ammonium sulfate.

The hybridoma that produces mAb 6G10 was deposited on Aug. 2, 1990, under accession No. HB 10519 at the American Type Culture Collection (ATCC), 12301 Parklawn Drive, Rockville, Md., U.S.A.

Monoclonal and polyclonal antibodies. For blocking lymphocyte adhesion to endothelial cells, all mAb's were added to either endothelial cells or lymphocytes at a final concentration of 10–50 μg/ml or 50% supernatant in the adhesive buffer and incubated for 30 minutes at 37° C. After 2 washes, cells were used in the adhesion assay as described above. For immunofluorescence tests, endothelial cells or CHO cells transfected with cDNAs encoding human VCAM-1, ICAM-1, ELAM-1, or CD4 (gifts of R. Lobb and J. Harlan) were propagated on tissue culture 8-chamber slides (VWR). Live, or ice-cold acetone or paraformaldehyde-fixed (2% in PBS) cells were preblocked with 3% goat serum in PBS, and incubated with mAb or polyclonal antibodies for 2 hr at room temperature. After washes, cells were incubated with FITC-labeled goat anti-mouse Ig antibodies for 30 min at room temperature, washed and mounted for analysis by immunofluorescent microscopy using a Bio-Rad laser scanning confocal microscope and image analysis software. The following antibodies were used: anti-ICAM (RR1/1, a gift from R. Rothlein), anti-LFA-1 (60.3, a gift from P. Beatty), anti-CD44 (Hutch-1), anti-lymph node addressin (MECA-79, a gift of P. Streeter and E. Butcher), anti-class II MHC (HB10a, a gift of E. Clark), anti-factor VIII (Calbiochem), anti-IL-4 (Immunex), and anti-human VCAM-1 (4B9, a gift of J. Harlan; and E1/6, a gift of M. Bevilaqua). In contrast to cultured endothelial cells from macaque aorta, microvascular endothelial cells showed no detectable labeling by polyclonal antibodies to factor VIII, which was in complete agreement with reports of negative labeling with factor-VIII antibodies of cultured microvascular endothelial cells from rat peripheral nodes (36–38).

Citations

1. Gallatin, W. M., et al., A cell-surface molecule involved in organ-specific homing of lymphocytes, *Nature* 304:30, 1983.
2. Holzmann, B., et al., Identification of a murine Peyer's patch-specific lymphocyte homing receptor as an integrin molecule with an α chain homologous to human VLA 4, *Cell* 56:37, 1989.
3. Duijvestijn, A., and A. Hamann, Mechanisms and regulation of lymphocyte migration, *Immunol. Today* 10:23, 1988.
4. Gallatin, W. M., et al., Lymphocyte homing receptors, *Cell* 44:673, 1986.
5. Yednock, T. A., and S. D. Rosen, Lymphocyte homing, *Adv. Immunol.* 44:313, 1989.
6. Woodruff, J. J., and L. M. Clarke, Specific cell-adhesion mechanisms determining migration pathways of recirculating lymphocytes, *Ann. Rev. Immunol.* 5:201, 1987.
7. Hamann, A., et al., Evidence for an accessory role of LFA-1 in lymphocyte-high endothelium interaction during homing, *J. Immunol.* 140:693, 1988.

8. Rothlein, R., et al., A human-intercellular adhesion molecule (ICAM-1) distinct from LFA-1, *J. Immunol.* 137:1270, 1986.
9. Marlin, S. D., and T. A. Springer, Purified intercellular adhesion molecule-1 (ICAM-1) is a ligand for lymphocyte function-associated antigen-1(LFA-1), *Cell* 51:813, 1987.
10. Cotran, R. S., New roles for the endothelium in inflammation and immunity, *Am. J. Pathol.* 129:407, 1987.
11. Jalkanen, S., et al., A distinct endothelial cell recognition system that controls lymphocyte traffic into inflamed synovium, *Science* 233:556, 1986.
12. Madri, J. A., et al., Matrix-driven cell size change modulates aortic endothelial cell proliferation and sheet migration, *Am. J. Pathol.* 132:18, 1988.
13. Pals, S. T., et al., Mechanisms of human lymphocyte migration and their role in the pathogenesis of disease, *Immunol. Rev.* 108:111, 1989.
14. Pober, J. S., Cytokine-mediated activation of vascular endothelium. Physiology and pathology, *Am. J. Pathol.* 133:426, 1988.
15. Duijvestijn, A. M., et al., Interferon-γ regulates an antigen specific for endothelial cells involved in lymphocyte traffic, *Proc. Natl. Acad. Sci. USA* 83:9114, 1986.
16. Pohlman, T. H., and J. M. Harlan, Human endothelial cell response to lipopoly-saccharide, interleukin-1, and tumor necrosis factor is regulated by protein synthesis, *Cell. Immunol.* 119:41, 1989.
17. Bevilaqua, M. P., et al., Interleukin 1 acts on cultured human vascular endothelium to increase the adhesion of polymorphonuclear leukocytes, monocytes, and related leukocyte cell lines, *J. Cltn. Invest.* 76:2003, 1985.
18. Cavender, D. E., et al., Interleukin 1 increases the binding of human B and T lymphocytes to endothelial cell monolayers, *J. Immunol.* 136:203, 1986.
19. Bevilacqua, M. P., et al., Identification of an inducible endothelial-leucocyte adhesion molecule, *Proc. Nati. Acad. Sci. USA* 84:9238, 1987.
20. Yu, C. L., et al., Human gamma interferon increases the binding of T lymphocytes to endothelial cells, *Clin. Exp. Immunol.* 62:554, 1985.
21. Yu, C. L., et al., Effects of bacterial lipopolysaceharide on the binding of lymphocytes to endothelial cell monolayers, *J. Immunol.* 136:569, 1986.
22. Cavender, D. E., et al., Stimulation of endothelial cell binding of lymphocytes by tumor nectosis factor, *J. Immunol.* 139:1855, 1987.
23. Issekutz, T. B., and J. M. Stoltz, Stimulation of lymphocyte migration by endotoxin, tumor necrosis factor, and interferon, *Cell. Immunol.* 120:165, 1989.
24. Issekutz, T. B., Effects of six different cytokines on lymphocyte adherence to microvascular endothelium and in vivo lymphocyte migration in the rat, *J. Immunol.* 144:2140, 1990.
25. Kalaaji, A. N., et al., Enhancement of lymphocyte localization in skin sites of sheep by tumor necrosis factor alpha, *Immunol. Letters* 23:143–148, 1989.
26. Stoolman, L. M, Adhesion molecules controlling lymphocyte migration, *Cell* 56:907, 1989.
27. Dustin, M. L., and T. S. Springer, Lymphocyte function-associated antigen-1 (LFA-1) interaction with intercellular adhesion molecule-1 (ICAM-1) is one of at least three mechanisms for lymphocyte adhesion to cultured endothelial cells, *J. Cell Biol.* 107:321, 1988.
28. Price, G. E., and M. P. Bevilaqua, An inducible endothelial cell surface glycoprotein mediates melanoma adhesion, *Science* 246:1303, 1989.
29. Osborn, L., et al., Direct cloning of vascular cell adhesion molecule 1, a cytokine-induced endothelial protein that binds to lymphocytes, *Cell* 59:1203, 1989.
30. EIIces, M. J., et al., VCAM-1 on activated endothelium interacts with the leucocyte integrin VLA-4 at a site distinct from the VLA-4/fibronectin binding site, *Cell* 60:577, 1990.
31. Streeter, P. R., et al., Immunohistologic and functional characterization of vascular addressin involved in lymphocyte homing into peripheral lymph nodes, *J. Cell Biol.* 107:1853, 1988.
32. Streeter, P. R., et al., A tissue-specific endothelial cell molecule involved in lymphocyte homing, *Nature* (Lond.) 331:41, 1988.
33. Sarvetnick, N., et al., Insulin-dependent diabetes mellitus induced in transgenic mice by ectopic expression of class II MHC and interferongamma, *Cell* 52:773, 1988.
34. Hendriks, H. R., et al., Rapid decrease in lymphocyte adherence to high endothelial venules in lymph nodes deprived of afferent lymphatic vessels, *Eur. J. Immunol.* 17:1691, 1987.
35. Williams, S. K., Isolation and Culture of Microvessel and Large-Vessel Endothelial Cells; Their Use in Transport and Clinical Studies, in Macrovascular Perfusion and Transport in Health and Disease, McDonagh, ed.; Karger, Basel, p. 204, 1987.
36. Kumar, S., et al., Heterogeneity in endothelial cells from large vessels and microvessels, *Differentiation* 36:57, 1987.
37. Ager, A., Isolation and culture of high endothelial cells from rat lymph nodes, *J. Cell Sci.* 87:133, 1987.
38. Ise, Y., et al., Molecular mechanisms underlying lymphocyte recirculation. I. Functional, phenotypical and morphological characterization of high endothelial cells cultured in vitro, *Eur. J. Immunol.* 18:1235, 1988.
39. Gallatin, W. M., et al., Selective replication of simian immunodeficiency virus in a subset of CD4+ lymphocytes, *Proc. Natl. Acad. Sci. USA* 86:3301, 1989.
40. Kennett, R. H., Fusion Protocols. Fusion by Centrifugation of Cell Suspended in Polyethylene Glycol, in Monoclonal Antibodies. Hybridomas: a New Dimension in Biological Analysis, R. H. Kennett et al., eds.; Plenum Press, New York, p. 365, 1980.
41. Monroe, J. G., et al., Lymphokine regulation of inflammatory process: interleukin-4 stimulates fibroblast proliferation, *Clin. Immunol. Immunopathol.* 49:292, 1988.
42. Park, L., et al., Characterization of the human B cell stimulatory factor 1 receptor, *J. Exp. Med.* 166:476, 1987.
43. Park, L. S., et al., Characterization of the high-affinity cell-surface receptor for murine B-cell-stimulating factor 1, *Proc. Nati. Acad. Sci. USA* 84:1669, 1987.
44. Lowenthal, J. W., et al., Expression of high affinity receptors for murine interleukin 4 (BSF-1) on hemopoietic and nonhemopoietic cells, *J. Immunol.* 140:456, 1988.
45. Elias, J. A., et al., A synergistic interaction of IL-6 and IL-1 mediates the thymocyte-stimulating activity produced by recombinant IL-1-stimulated fibroblasts, *J. Immunol.* 142:509, 1989.
46. Broxmeyer, H. E., et al., Synergistic effects of purified human and murine B cell growth factor 1/IL-4 on colony formation in vitro by hemopoietic progenitor cells, *J. Immunol.* 141:3852, 1988.
47. Makgoba, M. W., et al., Functional evidence that intercellular adhesion molecule-1 (ICAM-1) is a ligand for LFA-1-dependent adhesion in T cell-mediated cytotoxicity, *Eur. J. Immunol.* 18:637, 1988.

48. Pober, J. S., et al., Ia expression by vascular endothelium is inducible by activated T cells and by human γ-interferon, *J. Exp. Med.* 167:1339, 1983.
49. Collins, T., et al., Recombinant human tumor necrosis factor increases mRNA levels and surface expression of HLA-A,B antigens in vascular endothelial cells and dermel fibroblasts in vitro, *Proc. Natl. Acad. Sci. USA* 83:446, 1986.
50. Lapiere, L. A., et al., Three distinct classes of regulatory cytokines control endothelial cell MHC antigen expression, *J. Exp. Med.* 167:794, 1988.
51. Gimbrone, M. A., Jr., et al., Endothelial interleukin-8: a novel inhibitor of leukocyte-endothelial interactions, *Science* 246:1601, 1989.
52. Thornhill, M. H., et al., IL-4 increases human cell adhesiveness for T cells but not for neutrophils, *J. Immunol.* 144:3060, 1990.
53. Issekutz, T. B., et al., Role of interferon in lymphocyte recruitment into the skin, *Cell. Immunol.* 99:322, 1986.
54. Issekutz, T. B., et al., Lymphocyte recruitment in delayed-type hypersensitivity. The role of gamma-interferon, *J. Immunol.* 140:2989, 1988.
55. Hughes, C. C. W., et al., Adhesion of lymphocytes to cerebral microvascular cells: effects of interferon-γ, tumor necrosis factor and interleukin-1, *Immunology* 64:677, 1986.
56. Oppemheimer-Marks, N., and M. Ziff, Migration of lymphocytes through endothelial cell monolayers: augmentation by interferon-$_\gamma$, *Cell. Immunol.* 114:307, 1988.
57. Damle, N. K., and L. V. Doyle, Ability of human T lymphocytes to adhere to vascular endothelial cells and augment endothelial permeability to macromolecules is linked to their state of post-thymic maturation, *J. Immunol.* 144:1233, 1990.
58. Paul, W. E., and J. Ohara, B-cell stimulatory factor 1/interleukin 4, *Ann. Rev. Immunol.* 5:429, 1987.
59. Noelle, R., et al., Increased expression of Ia antigens on resting B cells: an additional role for B-cell growth factor, *Proc. Natl. Acad. Sci. USA* 91:6149, 1984.
60. McHeyzer-Williams, M. G., Combinations of interleukins 2, 4 and 5 regulate the secretion of murine immunoglobulin isotypes, *Eur. J. Immunol.* 19:2025, 1989.
61. Tsuji, K., et al., Synergistic action of phorbol ester and IL-3 in the induction of "connective tissue-type" mast cell proliferation, *J. Immunol.* 144:678, 1990.
62. Wankowicz, Z., et al., Synergy between tumor necrosis factor alpha and interleukin-1 in the induction of polymorphonuclear leukocyte migration during inflammation, *J. Leukoc. Biol.* 43:349, 1988.
63. Rabin, E. M., et al., Interferon-γ inhibits the action of B cell stimulatory factor (BSF)-1 on resting B cells, *J. Immunol.* 137:1573, 1986.
64. Vercelli, D., et al., IL-4 inhibits the synthesis of IFN-gamma and induces the synthesis of IgE in human mixed lymphocyte cultures, *J. Immunol.* 144:570, 1990.
65. Dexter, T. M. et al., *J. Cell. Physiol.* 91:335–344, 1977.
66. Gartner, S. M., and H. S. Kaplan, *Proc. Natl. Acad. Sci. USA* 77:4756–4761, 1980.
67. Roberts, R. A. et al., *Nature* 326:403–405, 1987.
68. Bentley, S. A., *Exp. Hematol.* 9:303–312, 1981.
69. Elices, M. J. et al., *Cell* 60:577, 1990.
70. Civin, C. I. et al., *J. Immunol.* 133:157–162, 1984.
71. Schuening, F. et al., *Transplantation* 44:607, 1987.
72. Sandmaier, B. M., Storb, R., Appelbaum, F. R., Gallatin, W. M. (1990) *Blood*, in press.
73. Fischer, A. et al., *Transplantation* 3:204, 1988.

While the present invention has been described in conjunction with a preferred embodiment, one of ordinary skill in the art after reading the foregoing specification will be able to effect various changes, substitutions of equivalents, and alterations to the subject matter set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A method of isolating or immunoselecting bone marrow stromal cells that express VCAM-1 comprising the steps of contacting cells from bone marrow with an antibody that specifically binds to VCAM-1 and isolating or immunoselecting stromal cells that bind to the antibody.

2. The method of claim 1 wherein the antibody that specifically binds to VCAM-1 is selected from the group consisting of monoclonal antibodies and antigen-binding fragments of said monoclonal antibodies that specifically binds to an epitope recognized by 6G10 monoclonal antibody produced by hybridoma ATCC No. HB 10519.

3. A method of detecting bone marrow stromal cells that express VCAM-1 comprising the steps of contacting cells from bone marrow with an antibody that specifically binds to VCAM-1 and detecting stromal cells that bind to the antibody.

4. The method of claim 1 wherein the antibody that specifically binds to VCAM-1 is selected from the group consisting of monoclonal antibodies and antigen-binding fragments of said monoclonal antibodies that specifically bind to an epitope recognized by 6G10 monoclonal antibody produced by hybridoma ATCC No. HB 10519.

* * * * *

UNITED STATES PATENT AND TRADEMARK OFFICE
CERTIFICATE OF CORRECTION

PATENT NO. : 5,827,670
DATED : October 27, 1998
INVENTOR(S) : Masinovsky et al.

It is certified that error appears in the above-identified patent and that said Letters Patent is hereby corrected as shown below:

<u>Title page,</u>
Related U.S. Application Data,
Line 2, Serial No. 51,445 according to our records is not "abandoned", replace with -- pending --.

OTHER PUBLICATIONS,
Under Calvender *et al.*, replace "Calvender *et al.*" with -- Cavender *et al.* --.
Under Civin *et al.*, replace "Antgenic" with -- Antigenic --.
Under Damle *et al.*, replace "144:1223-1240" with -- 144:1233-1240 --.
Under Elices *et al.*, replace "integrin VKA-4" with -- integrin VLA-4 --.
Under Galea, replace "Allogeneic Cells" with -- Allogeneic Endothelial Cells --.
Under Gallatin *et al.*, replace "oragan-specific" with -- organ-specific --.
Under Hart *et al.*, replace "tmmor" with -- tumor --.
Under Holzmann *et al.*, replace "Identificatin" with -- Identification --.
Under Holzmann *et al.*, replace "as in integrin" with -- as an integrin --.
Under Kennett, replace "pp. 35-367" with -- pp. 365-367 --.
Under Makgoba *et al.*, replace "(ICAM)" with -- (ICAM-1) --.
Under Makgoba *et al.*, replace "adhesion T-cell" with -- adhesion in T-cell --.
Under Monroe *et al.*, replace "process" with -- processes --.
Under Mountain *et al.*, replace "Biotech. Ben. Eng. Rev." with -- Biotech. Gen. Eng. Rev. --.
Under Osborn *et al.*, replace "indothelial protein" with -- endothelial protein --.
Under Zanjani *et al.*, replace "Homeless" with -- "Homeless" --.
Under Schaffer, replace "imflammatory" with -- inflammatory --.
Under Thornhill *et al.*, replace "neutrophilis" with -- neutropils --.
Under Wetzler *et al.*, replace "TNF-$\beta$" with -- TGF-$\beta$ --.

UNITED STATES PATENT AND TRADEMARK OFFICE
CERTIFICATE OF CORRECTION

PATENT NO. : 5,827,670
DATED : October 27, 1998
INVENTOR(S) : Masinovsky et al.

It is certified that error appears in the above-identified patent and that said Letters Patent is hereby corrected as shown below:

Column 2,
Line 34, replace "vascular addressing" with -- vascular addressins --.

Column 9,
Line 52, replace "12-2 hr" with -- 12-24 hr --.

Column 14,
Line 47, replace "370° C" with -- 37° C --.

Column 17,
Line 32, replace "J. Cltn. Invest." with -- J. Clin. Invest. --.
Line 37, replace "Proc. Nati. Acad. Sci." with -- Proc. Natl. Acad. Sci. --.
Line 46, replace "nectosis" with -- necrosis --.

Column 18,
Line 4, replace "Ellces, M.J." with -- Elices, M.J. --.
Line 51, replace "Proc. Nati. Acad. Sci." with -- Proc. Natl. Acad. Sci. --.

Column 19,
Line 7, replace "Proc. Nati. Acad. Sci." with -- Proc. Natl. Acad. Sci. --.

Signed and Sealed this

Twenty-fifth Day of December, 2001

Attest:

JAMES E. ROGAN
*Attesting Officer*  *Director of the United States Patent and Trademark Office*